US011523853B2

(12) United States Patent
Kinane et al.

(10) Patent No.: US 11,523,853 B2
(45) Date of Patent: Dec. 13, 2022

(54) METHOD AND APPARATUS FOR FIXATION

(71) Applicant: Materialise N.V., Leuven (BE)

(72) Inventors: Billy Kinane, Dublin (IE); Inge Famaey, Leuven (BE); Dieter Vangeneugden, Leuven (BE); Nils Faber, Leuven (BE)

(73) Assignee: Materialise N.V., Leuven (BE)

( * ) Notice: Subject to any disclaimer, the term of this patent is extended or adjusted under 35 U.S.C. 154(b) by 0 days.

(21) Appl. No.: 16/977,046

(22) PCT Filed: Mar. 7, 2019

(86) PCT No.: PCT/US2019/021209
§ 371 (c)(1),
(2) Date: Aug. 31, 2020

(87) PCT Pub. No.: WO2019/173627
PCT Pub. Date: Sep. 12, 2019

(65) Prior Publication Data
US 2021/0038275 A1    Feb. 11, 2021

Related U.S. Application Data

(60) Provisional application No. 62/640,134, filed on Mar. 8, 2018.

(51) Int. Cl.
*A61B 17/86* (2006.01)
*A61B 17/00* (2006.01)

(52) U.S. Cl.
CPC ........ *A61B 17/8685* (2013.01); *A61B 17/866* (2013.01); *A61B 2017/00477* (2013.01); *A61B 2017/00526* (2013.01)

(58) Field of Classification Search
CPC ... A61B 17/844; A61B 17/8685; A61B 17/84; A61B 17/866; A61B 2017/00477; A61B 2017/00526
See application file for complete search history.

(56) References Cited

U.S. PATENT DOCUMENTS

| | | | |
|---|---|---|---|
| 6,695,844 B2 | 2/2004 | Bramlet et al. | |
| 2008/0255618 A1* | 10/2008 | Fisher | A61B 17/7064 606/247 |
| 2010/0057141 A1* | 3/2010 | Abdelgany | A61B 17/8685 606/310 |
| 2010/0168751 A1* | 7/2010 | Anderson | A61B 17/7071 606/82 |

(Continued)

FOREIGN PATENT DOCUMENTS

WO    2011/163402 A1    12/2011

*Primary Examiner* — Kevin T Truong
*Assistant Examiner* — Diana Jones
(74) *Attorney, Agent, or Firm* — Ankur Garg

(57) ABSTRACT

The present disclosure relates to fixation devices. Certain embodiments provide a fixation device for insertion into bone. The fixation device includes a body comprising threads along an outer surface of the body. The fixation device includes one or more blades movably coupled to the body. The one or more blades are configured to move between at least a first position and a second position. In the first position, the one or more blades are retracted into the body. In the second position, the one or more blades are deployed out of the body for insertion into the bone.

14 Claims, 31 Drawing Sheets

(56) References Cited

U.S. PATENT DOCUMENTS

| | | | |
|---|---|---|---|
| 2012/0197315 A1* | 8/2012 | Kim | A61B 17/7032 606/305 |
| 2014/0188179 A1* | 7/2014 | McCormick | A61B 17/86 606/301 |
| 2015/0045841 A1* | 2/2015 | Oglaza | A61B 17/7001 606/322 |
| 2017/0258498 A1* | 9/2017 | Redmond | A61B 17/7055 |

* cited by examiner

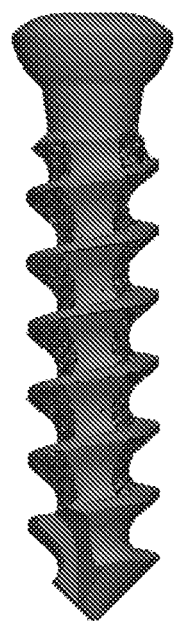
FIG. 2A
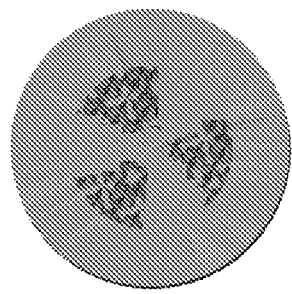 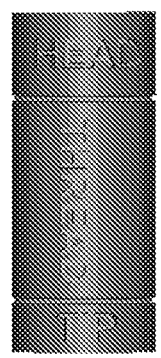 
FIG. 2B  FIG. 2C  FIG. 2D

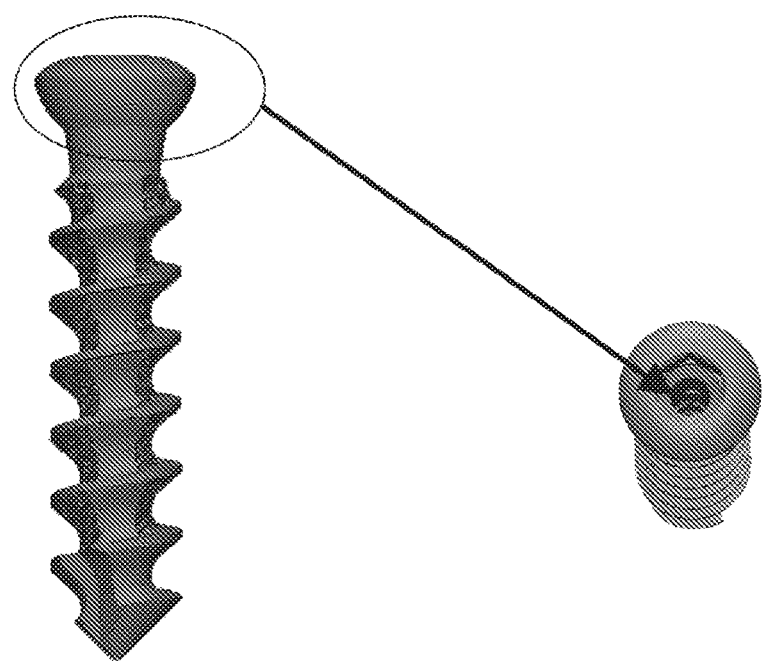
FIG. 3A  FIG. 3E
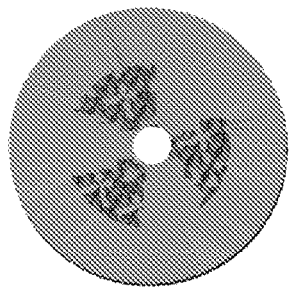
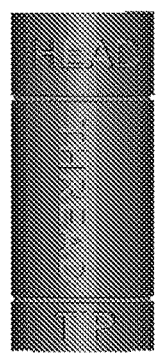
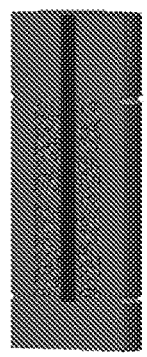
FIG. 3B  FIG. 3C  FIG. 3D

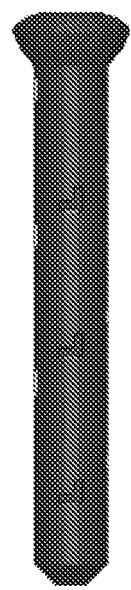
FIG. 5A  FIG. 5B
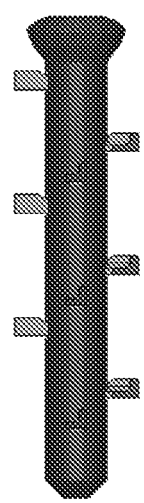
FIG. 5C  FIG. 5D

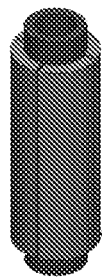
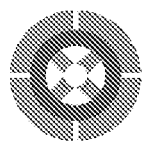
FIG. 6A          FIG. 6B
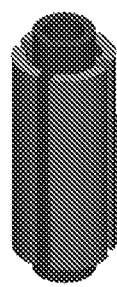
FIG. 6C          FIG. 6D

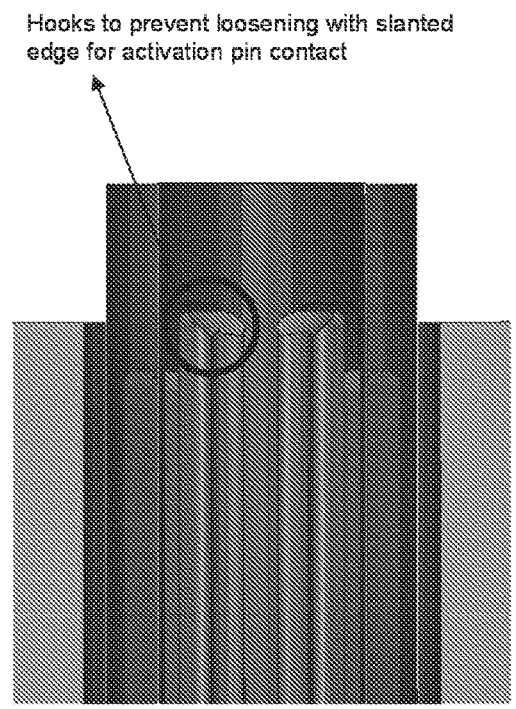
FIG. 6E
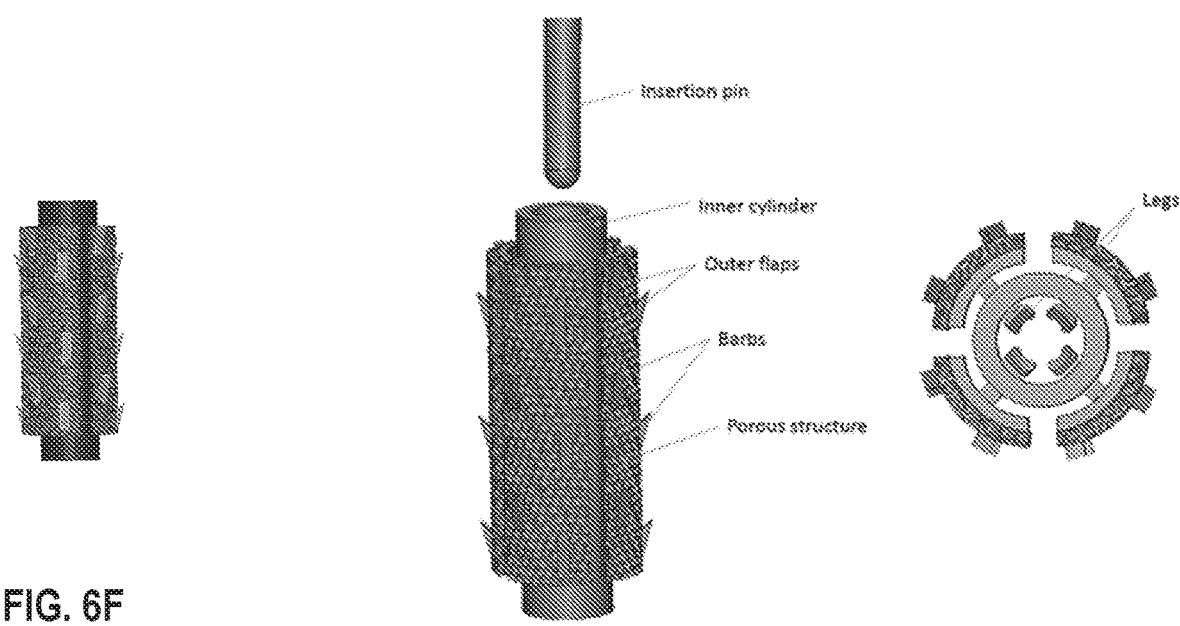
FIG. 6F
FIG. 6G

METHOD AND APPARATUS FOR FIXATION

CROSS-REFERENCE TO RELATED APPLICATIONS

This application claims the benefit of U.S. Provisional Patent No. 62/640,134, filed Mar. 8, 2018. The content of the provisional application is hereby incorporated by reference in its entirety.

BACKGROUND OF THE INVENTION

Field of the Invention

The present disclosure relates to fixation devices. More particularly, the present disclosure relates to fixation devices, such as for fixation in bone.

Description of the Related Technology

Bone fixation devices are often used to fixate implants to bone or to repair bone fractures. For example, screws, locking screws, non-locking screws, plugs, intramedullary nails, etc. may all be examples of bone fixation devices that can be used separately or together to repair a bone fracture, to reduce bone fragments after an osteotomy or to fixate an implant or other object to bone of a patient.

Typically, bone fixation devices are designed with a focus solely on unidirectional (i.e., axial) pull-out resistance. However, in most circumstances, physiological loading forces of bone fixation devices are not strictly unidirectional, but rather multidirectional.

Further, typical bone fixation devices and techniques are designed with a focus solely on initial mechanical fixation. Most bone fixation techniques do not offer any additional long-term fixation such as biological ingrowth of bone to the bone fixation device. This is a shortcoming because screw loosening is a known leading cause of implant failure.

In addition, typical bone fixation techniques generally require a user to apply significant force during bone insertion (such as the insertion torque for screws). Also, bone fixation mechanisms that attempt to increase resistance to multidirectional loading generally generate larger friction during bone insertion.

One type of bone fixation device is a dynamic hip screw (DHS) system typically used for the treatment of inter-trochanteric fractures. A DHS system typically works by inserting a lag screw into a patient's proximal femur such as from the lateral side and through the femoral neck to a position where the screw head of the lag screw sits at a distance from the cortex of the femoral head. Failure of such a conventional DHS system is common, with 8-13% of cases requiring revision. One common cause of failure is cut-out where the lag screw (e.g., tip of the lag screw) migrates and cuts-out through the cortex of the femoral head or the femoral neck. In particular, the lag screw may move within the bone, thereby resulting in cut-out and failure of the DHS system.

Accordingly, improved bone fixation devices and techniques are needed.

SUMMARY

Certain embodiments provide a fixation device for insertion into bone. The fixation device includes a body comprising threads along an outer surface of the body. The fixation device includes one or more blades movably coupled to the body. The one or more blades are configured to move between at least a first position and a second position. In the first position, the one or more blades are retracted into the body. In the second position, the one or more blades are deployed out of the body for insertion into the bone.

Certain embodiments provide a method of manufacturing a fixation device comprising a porous structure. The method includes generating a piece of material comprising a porous structure using additive manufacturing. The method further includes cutting the material to form the fixation device.

BRIEF DESCRIPTION OF THE DRAWINGS

FIGS. 2A-2D provide examples of a screw with a porous structure.

FIGS. 3A-3E provide examples of a screw with a porous structure and a cavity.

FIGS. 5A-5E provide examples of a fixation device with puncturing elements.

FIGS. 6A-6G provide examples of a fixation device with expandable elements.

DETAILED DESCRIPTION OF INVENTION

Figure 1A:
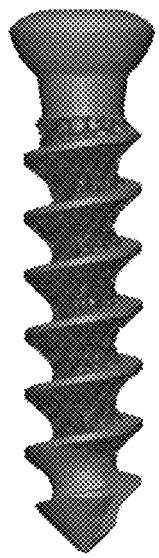
FIGS. 1A-1H provide examples of a screw with a porous structure.
Figure 1E:
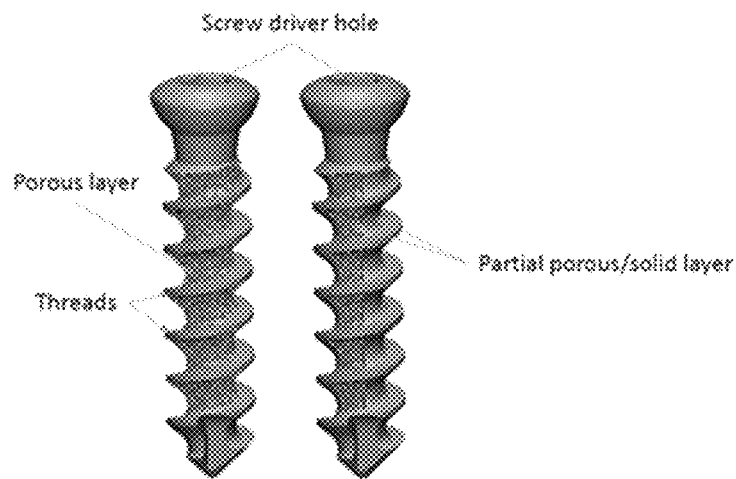
Figure 1B:
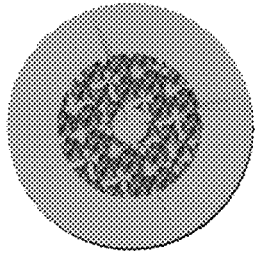
Figure 1C:
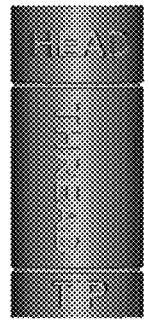
Figure 1D:
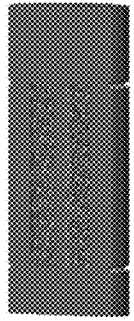
Figure 1H:
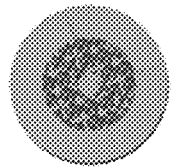
Figure 1F:
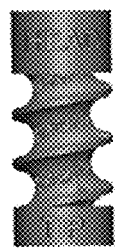
Figure 1G:
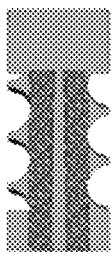
Figure 4A:
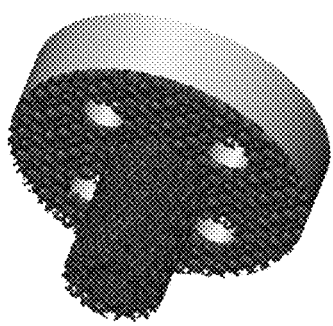
FIGS. 4A-4F provide examples of a plug with a porous structure and a cavity.
Figure 4B:
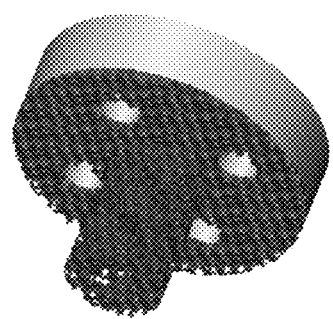
Figure 4C:
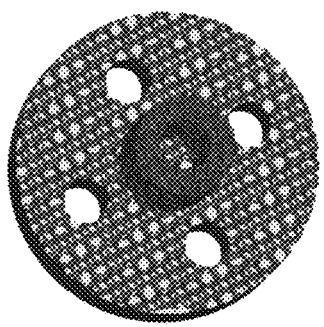
Figure 4D:
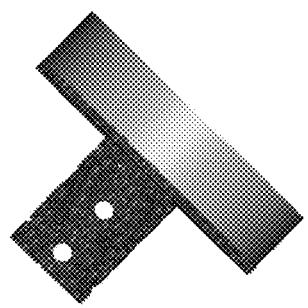
Figure 4E:
Figure 4F:
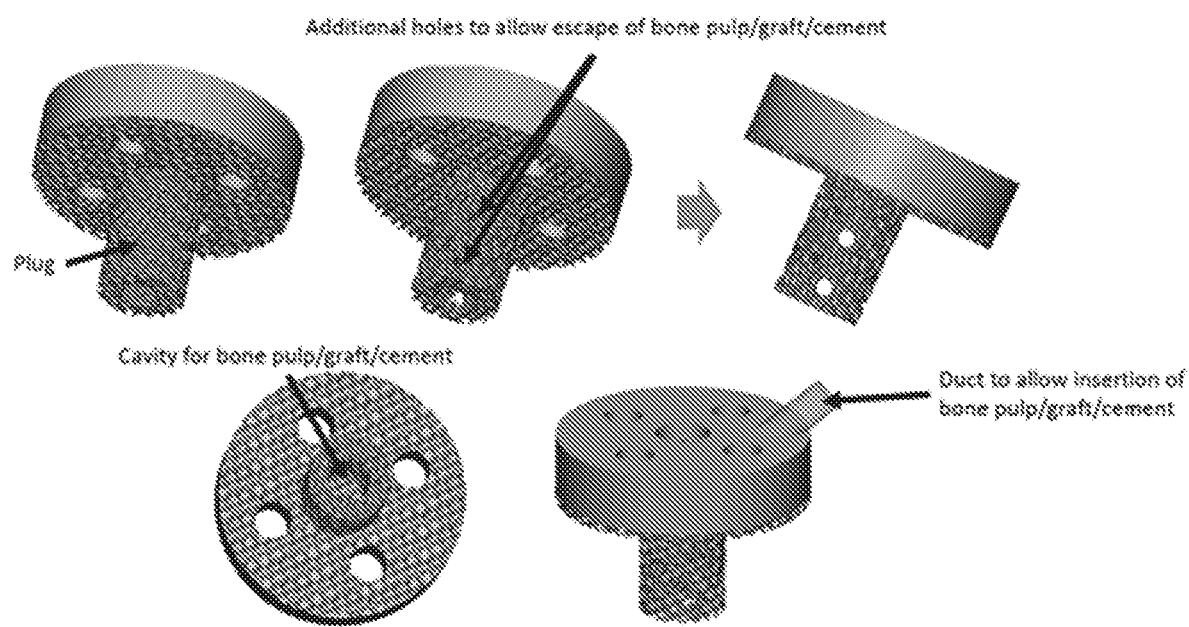
Figure 5E:
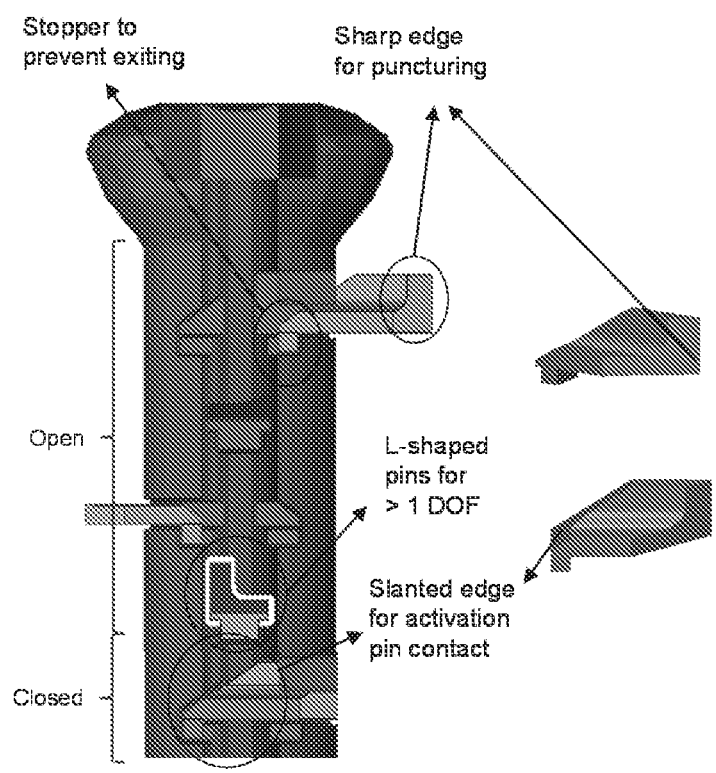
Figure 7A:
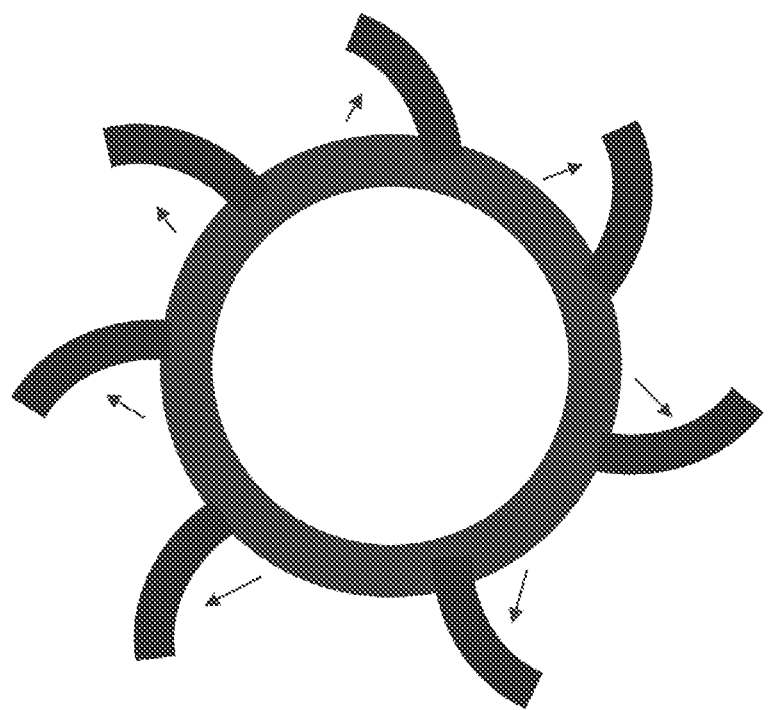
FIGS. 7A-7B provide examples of a fixation device with expandable elements.
Figure 7B:
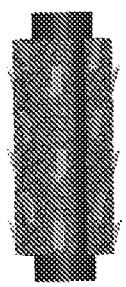
Figure 8A:
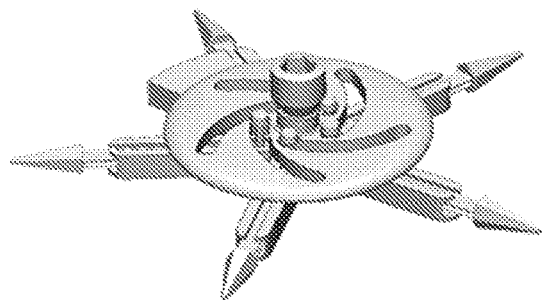
FIGS. 8A-8D provide examples of a fixation device with spike arms.
Figure 8B:
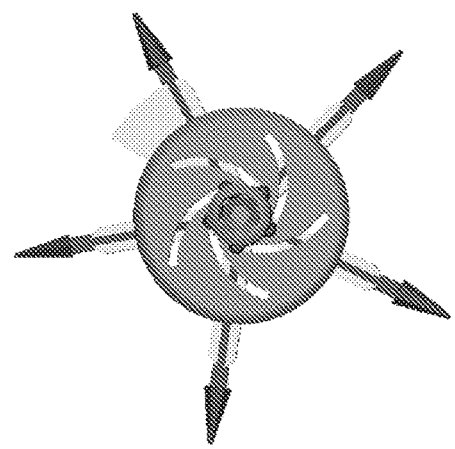
Figure 8C:
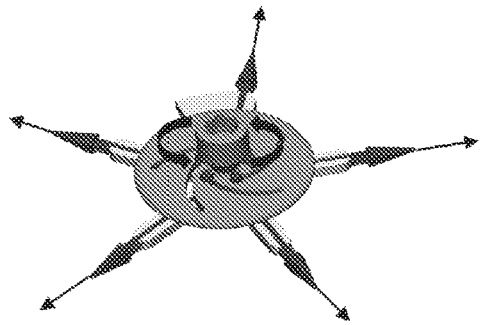
Figure 8D:
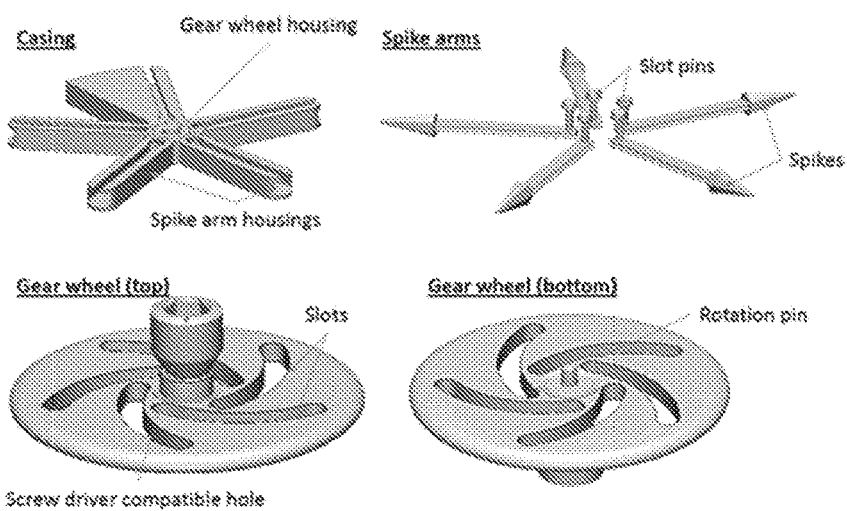

The following description and the accompanying figures are directed to certain specific embodiments. The embodiments described in any particular context are not intended to limit this disclosure to the specified embodiment or to any particular usage. Those of skill in the art will recognize that the disclosed embodiments, aspects, and/or features are not limited to any particular embodiments. For example, reference to "a" layer, component, part, etc., may, in certain embodiments, refer to "one or more."

Certain embodiments herein provide bone fixation devices and techniques that can cope with the complex loading scenarios, such as those that actually occur in vivo. Certain embodiments herein provide bone fixation devices and techniques that provide biological ingrowth. Certain embodiments herein provide bone fixation devices and techniques that do not compromise between multiaxial loading resistance and ease of insertion.

It should be noted that one of the skill in the art will understand that one or more of the embodiments described herein, or portions of embodiments, may be combined such as to provide the benefits described herein. Further, though certain embodiments describe fixation techniques and devices for bone, they may also be applicable to other uses, such as non-medical uses. In addition, one or more of the embodiments described herein may be used in a specialized fixation device (such as screws, plugs and others) or in an implant itself (supplementing or replacing specialized fixation devices).

Certain embodiments provide improved long-term biological fixation. For example, certain embodiments provide fixation devices with porous material that enables/promotes bone ingrowth into the bone fixation device. In another example, certain embodiments provide one or more cavities in a fixation device in which bone graft material can be inserted.

Certain embodiments provide improved mechanical fixation. For example, certain embodiments provide one or more cavities in the fixation device in which bone cement or other material can be inserted. In another example, certain embodiments provide moving elements in the fixation device that when deployed can puncture the bone and rest seated for bone fixation. In another example, certain embodiments provide elements in the fixation device that when deployed expand the size of the non-deployed device and compress the bone.

In another example, certain embodiments provide elements in the fixation device that when deployed both puncture and compress the bone. In another example, certain embodiments provide elements in the fixation device that when deployed anchor behind cortical bone. In another example, certain embodiments provide elements, such as puncturing elements (e.g., blades), in the fixation device that when deployed puncture the bone over a relatively large surface area/volume, thereby better resisting movement of the fixation device in the bone, such as in the direction that load is applied to the fixation device due to activity/movement of the patient. The volume occupied by the fixation device is expanded, accordingly, when the elements in the fixation device are deployed. In certain embodiments, the elements, when deployed, are oriented so as to provide resistance to movement in one or more directions of migration under weight-bearing loads. Certain such fixation devices may include a lag screw of a DHS system. Such a DHS system including such a lag screw may better prevent cut-out. Example materials used for the fixation device can include, but are not limited to, one or more of the following: titanium (e.g., commercially pure), titanium alloy (e.g., Ti6A14V (ELI)), magnesium based alloy, zinc based alloy, iron based alloy, poly lactic acid (PLDLA), bioactive glass fibers, polycaprolactone (PCL), polyhydroxyalkanoate (PHA), other bioresorbable materials, etc.

Certain embodiments provide improved promotion of bone remodeling. For example, certain embodiments provide a fixation device that is entirely or partially flexible, where load may be applied to the adjacent bone which promotes bone remodeling.

Certain embodiments provide improved post-processing techniques. For example, certain embodiments provide post-processing techniques to improve certain embodiments of the final product (e.g., a fixation device). For example, if the product contains screw thread, post-processing techniques can be applied to enhance the sharpness of the thread. Accordingly, in certain embodiments, a solution is proposed that combines a manufacturing method (e.g., additive manufacturing method) with a CNC-like post-processing technique.

Certain embodiments provide improved ease of insertion of the fixation device into bone. For example, certain embodiments provide assembly mechanisms, where fixation devices, such as screws, can be built up from separate smaller parts.

In one example, in each of the embodiments described, the fixation device includes a porous structure to allow bone ingrowth and to achieve improved long term fixation of the device. In certain embodiments, the method of producing porous structures on the subject fixation devices through the additive manufacturing process is new to each fixation device. In another example of certain embodiments described, the fixation device does not include a porous structure.

In certain embodiments, a fixation device includes one or more porous structures (e.g., as shown in FIGS. 1A-1H and FIGS. 2A-2D). In certain embodiments, the fixation device is a screw including one or more porous structures. The screw includes threads (e.g., to gain initial purchase in the host bone) and a screw driver hole (e.g., to allow insertion of the screw a hole in the screw compatible with a standard screw driver may be provided). One or more porous structures may be located anywhere on the screw body. Pore size of the porous structure may vary in different areas of the screw.

In certain embodiments, a fixation device includes one or more bone graft cavities (e.g., as shown in FIGS. 3A-3E and FIGS. 4A-4F). For example, one or more cavities may be formed on the fixation device in which bone material can be inserted. This may support the initial mechanical fixation with long-term biological fixation. This may lead to an improved fixation, which in turn decreases the risk of loosening and ultimate implant failure. In certain embodiments, a supply (e.g., channel) is provided in the fixation device via which the bone graft material can be inserted intraoperatively after the implant has been seated in its final position and has potentially already been fixated by the initial mechanical fixation device.

In certain embodiments, the fixation device is a screw (e.g., as shown in FIGS. 3A-3E) with a cannula and including one or more porous structures. The screw includes threads (e.g., to gain initial purchase in the host bone) and a screw driver hole (e.g., to allow insertion of the screw a hole in the screw compatible with a standard screw driver may be provided). One or more porous structures may be located anywhere on the screw body. Pore size of the porous structure may vary in different areas of the screw. The screw further includes a central hole (e.g., channel, cannula, etc.) such as in the screw core to allow insertion of the screw over a guide wire or application of bone pulp/bone cement.

In certain embodiments, the fixation device is a plug or stem (e.g., as shown in FIGS. 4A-4F) with a cannula and including one or more porous structures. The plug or stem may comprise an entity made from porous structure that protrudes into a premade bone cavity. In certain embodiments, the plug or stem can be attached to an essential part of an anatomy specific implant depending on the application. In certain embodiments, the plug or stem includes one or more holes or cavities to allow application of bone pulp/bone cement.

In certain embodiments, a fixation device includes one or multiple cavities (e.g., as shown in FIGS. 3A-3E and FIGS. 4A-4F) in the fixation device in which bone cement or other material can be inserted. For example, the primary mechanical fixation is supported by a second type of mechanical fixation (e.g., bone cement). The use of bone cement or other similar material has the additional benefit that it can seep into bone cavities or bone cracks and can therefore have a larger penetration depth than for example a standard bone screw. This leads to an improved fixation, which in turn decreases the risk of loosening and ultimate implant failure. In certain embodiments, a duct is provided in the fixation device via which the bone graft material can be inserted intraoperatively after the implant has been seated in its final position and has potentially already been fixated by the initial mechanical fixation mechanism.

In certain embodiments, the fixation device is a plug or stem (e.g., as shown in FIGS. 4A-4F) including one or more porous structures. The plug or stem may comprise an entity made from porous structure that protrudes into a premade bone cavity. In certain embodiments, the plug or stem can be attached to an essential part of an anatomy specific implant depending on the application. In certain embodiments, the plug or stem includes one or more holes or cavities to allow application of bone cement within the porous plug or stem. In certain embodiments, the plug or stem includes a duct to allow insertion of bone cement.

In certain embodiments, the fixation device comprises a puncturing device (e.g., as shown in FIGS. 5A-5E and FIGS. 8A-8D). For example, in certain embodiments, for mechanical fixation, the fixation device includes one or more moving puncturing elements that when deployed can puncture the bone and rest seated for bone fixation. Optionally these sharp puncturing elements can be retracted when it is needed to remove the fixation device. The deployment of the puncturing elements can be activated by various mechanisms such as by exerting pressure, applying a torque or other, in a way that can be manual, by use of a separate activation instrument (pin, internal screw, etc.) or other.

In certain embodiments, puncturing elements can have a larger penetration depth than traditional screw thread, leading to improved fixation.

In certain embodiments, traditional bone screws have the design restriction that the friction generated by the screw thread during device insertion into the bone must be low for ease of insertion. In contrast, in certain embodiments, puncturing elements can be hidden inside the fixation device and can be deployed after the device is seated in the bone. Therefore firstly, the state of the device during device insertion into the bone can be optimized for ease of insertion (low friction) and secondly, the state of the deployed device can be optimized for bone fixation (containing elements that would otherwise generate too much friction for device insertion into the bone). In certain embodiments, such design freedom allows the freedom to design the fixation device to offer resistance to multidirectional forces and bending moments, instead of the unidirectional fixation that is generally provided by standard fixation mechanisms. One of many possible ways to implement this is by making L-shaped puncturing elements. In certain embodiments, depending on the amount, size and length of the elements, the total bone contact surface can supersede that of traditional fixation mechanisms.

In certain embodiments, the fixation device (e.g., as shown in FIGS. 5A-5E) comprises one or more puncturing elements. In certain embodiments, a puncturing element can, when deployed, puncture the bone and remain seated for bone fixation. In particular, the fixation device is configured to transition between a deployed state where the one or more puncturing elements are extended/deployed from the fixation device to puncture and sit in bone and an un-deployed state where the one or more puncturing elements are retracted into the fixation device. A puncturing element may include a leg housed within the inner cylindrical cavity to receive an insertion pin. A puncturing element may comprise a porous structure. In certain embodiments, a puncturing element does not comprise a porous structure, such as for ease of retraction after implantation into bone. In certain embodiments, the fixation device includes an inner cylindrical cavity that houses the legs of the puncturing elements such that they are contained and prevented from dislocating from the device. In certain embodiments, the fixation device includes an activation mechanism for activating the puncturing elements such as by exerting pressure, applying a torque or other, in a way that can be manual, by use of a separate activation instrument (insertion pin, internal screw/bolt, etc.) or other.

In certain embodiments, the one or more puncturing elements of a fixation device comprise one or more blades. In certain embodiments, a blade refers to a substantially planar puncturing element (e.g., resembling a 2D geometric shape, albeit with some thickness). In certain embodiments, a substantially planar puncturing element is one with a surface area that substantially extends in more than one direction along more than one line path or curve. For example, a pin like puncturing element that substantially extends along a single line path or curve is not an example of a substantially planar puncturing element. In certain embodiments, such a blade has a geometric shape, such as a triangle. In certain aspects, a triangular shape is beneficial as the point of the triangle is suited for initially puncturing the bone over a reduced surface area of the bone, while the remaining portion of the triangle has a large surface area with which to contact the bone upon full deployment of the blade into bone.

In certain embodiments, a blade refers to a 3D shaped puncturing element. A 3D shaped puncturing element still includes a surface area that substantially extends in more than one direction along more than one line path or curve. However, instead of substantially sitting in a single plane, such as in a shape of a triangle, the 3D shaped puncturing element has features that are shaped and extend outside the single plane, such as resembling a 3D geometric object, such as a pyramid.

The use of blades in the fixation device may provide enhanced bone purchase when the blades are deployed into bone, such as over the use of pin like puncturing elements or threading of a screw alone.

Figure 18:
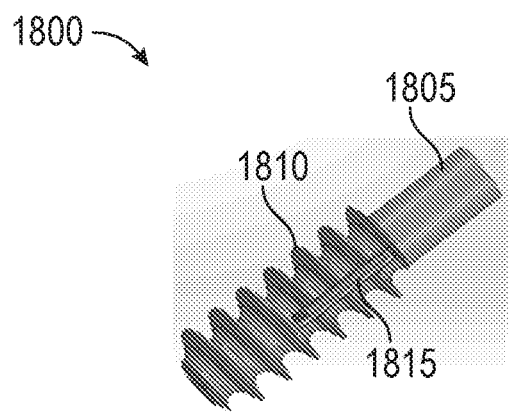
FIG. 18 illustrates an example of a fixation device comprising one or more blades in an un-deployed state, according to an embodiment.

FIG. 18 illustrates an example of a fixation device comprising one or more blades in an un-deployed state. As shown, fixation device 1800 includes a body shown as a shaft 1805, and a threaded portion 1810 along a portion of shaft 1805. Accordingly, fixation device 1800 comprises a screw or screw like fixation device. It should be noted that in some embodiments, fixation device 1800 does not include a threaded portion 1810, and may instead comprise a bolt or bolt-like fixation device. Further, fixation device 1800 includes a blade 1815. The blade 1815 is shown as retracted into the body of fixation device 1800. As shown, fixation device 1800 includes a slot or opening configured to allow the blade 1815 to be deployed from fixation device 1800. As shown, the slot has a length extending along the shaft 1805, which allows the blade 1815 to have a large surface area and still be able to deploy through the slot.

Figure 19:
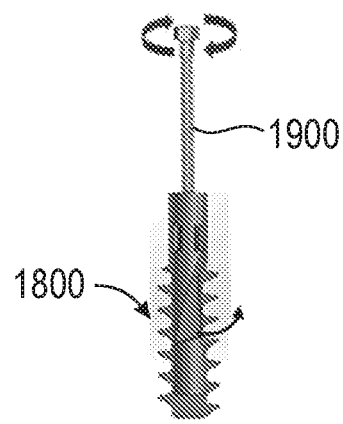
FIG. 19 illustrates interaction between a fixation device and an activation instrument, according to an embodiment.

FIG. 19 illustrates interaction between the fixation device 1800 and an activation instrument 1900. In particular, activation instrument 1900 is configured to interact with an (e.g., internal) activation mechanism of fixation device 1800 to deploy or retract blade 1815 from fixation device 1800. In certain aspects, the activation mechanism is configured to simultaneously deploy or retract multiple blades 1815. Accordingly, the blades 1815 are movably coupled to a body of fixation device 1800 and configured to move between at least a first position and a second position (e.g., the blades being retracted into the body and deployed out of the body). It should be noted that the activation instrument 1900 may be separate from, or integrated into the fixation device 1800. Where the activation instrument 1900 is integrated into the fixation device 1800, a length of the activation instrument 1900 may be reduced in some embodiments.

In certain embodiments, the activation mechanism comprises a bolt which is turned through a corresponding internal threaded section of the fixation device 1800. As the bolt advances it makes contact with the blades 1815 (e.g., directly, or via another component). These blades 1815 may be displaced from the inner housing of the fixation device 1800 by one or more elements configured for deformation (e.g., of slender limbs, elastically deforming members, etc.) coupled to the blades 1815, by means of a rotational hinge structure which attach them to the inner surface of the fixation device 1800, or by one or more elements configured for translational sliding coupled to the blades 1815 forming a translational sliding mechanism. Once the bolt is fully advanced, the blades 1815 should be in a fully deployed position.

In certain embodiments, it may be beneficial to orient blades 1815 substantially perpendicular to prevailing loads to be exerted on the fixation device 1800 after implantation in bone. Accordingly, in certain embodiments, one or more markings are added to a head of the fixation device 1800. The markings may be indicative of an orientation of the blades 1815 with respect to the head. A surgeon may then be able to determine the orientation of the blades 1815 with respect to the bone while screwing the fixation device 1800 into bone, such as to achieve a beneficial orientation.

In another embodiment, the head of the fixation device 1800 is configured to receive an activation instrument (e.g., a screwdriver) in only a single orientation (e.g., due to a shape of the head and/or of the activation instrument), such that an orientation of the activation instrument (e.g., as evidenced by a marker or shape of the activation instrument) is indicative of the orientation of the blades 1815 when inserted into the head of fixation device 1800.

Figure 20:
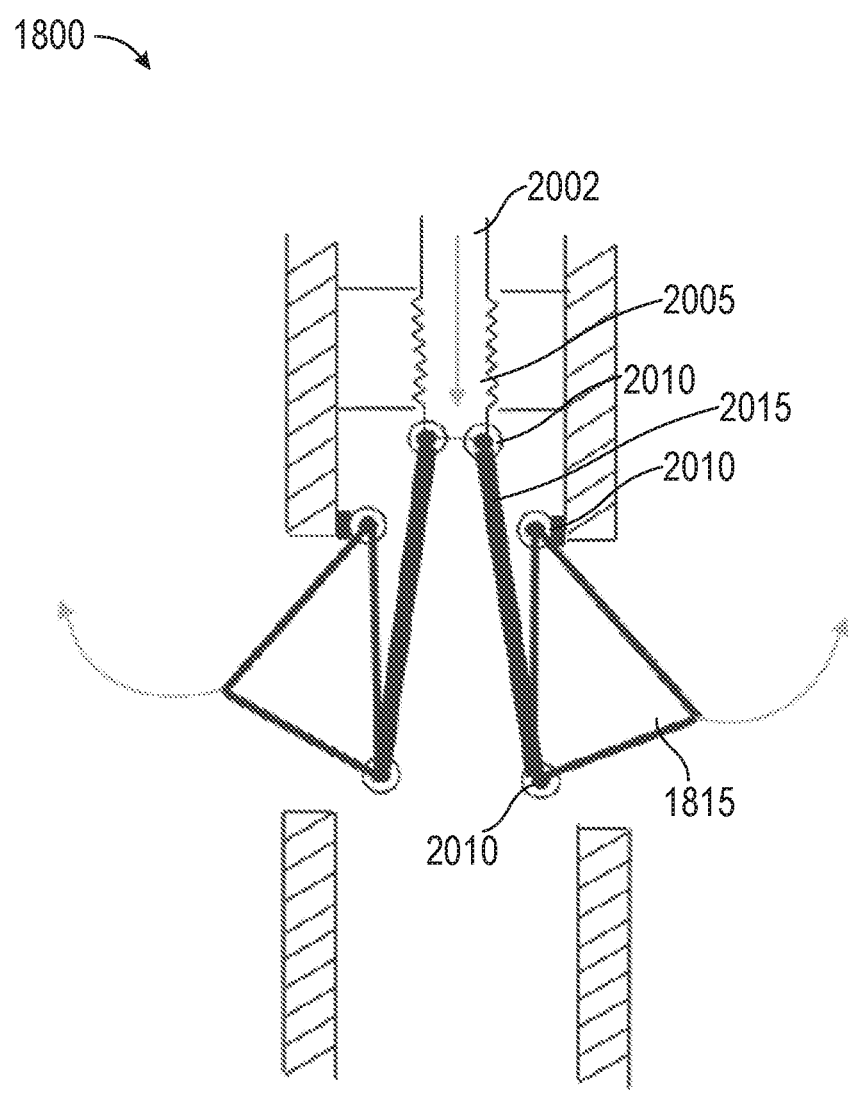
FIG. 20 illustrates an example activation mechanism of a fixation device, according to an embodiment.

FIG. 20 illustrates an example activation mechanism of fixation device 1800. As shown, the activation mechanism includes a coupling member also referred to as a shaft portion 2002 having a threaded region 2005. It should be noted that in some embodiments, the entire shaft portion 2002 is threaded. The shaft portion 2002 may be a portion of the activation instrument 1900, or may comprise a separate element configured to receive an activation instrument. The fixation device 1800 further includes a portion with complementary threads to the threads 2005. In particular, interaction of the complementary threads and threads 2005 allow for shaft portion 2002 to be moved by rotational force (e.g., using an activation instrument), while retaining position after being moved. Shaft portion 2002 is coupled by one or more hinges 2010 to one or more blades 1815. For example, each blade 1815 of fixation device 1800 is hingedly coupled to shaft portion 2002. In the example shown, blade 1815 is hingedly coupled to shaft portion 2002 via a connecting member 2015. In certain embodiments, the connecting member 2015 is a bar. In certain embodiments, not shown, blade 1815 is directly hingedly coupled to shaft portion 2002 without a connecting member. In certain embodiments, not shown, blade 1815 is hingedly coupled to shaft portion 2002 via more than one connecting member of the same or different shape/sizes.

In certain aspects, the hinge 2010 coupling shaft portion 2002 to blade 1815 and/or connecting member 2015 is attached by a socket-joint or other suitable means that allows shaft portion 2002 to rotate, but hinge 2010 not to rotate and only move translationally as shaft portion 2002 moves translationally.

As shown, one vertex or node of blade 1815 is hingedly coupled at a hinge 2010 to a (e.g., inner) wall of fixation device 1800, thereby allowing blade 1815 to rotate and deploy from inside fixation device 1800 to outside fixation device 1800 while remaining coupled to fixation device 1800. Further, a second vertex of blade 1815 is hingedly coupled to a first end of connecting member 2015 at a hinge 2010. A second end of connecting member 2015 is further hingedly coupled at a hinge 2010 to shaft portion 2002. Accordingly, blade 1815 is hingedly coupled to shaft portion 2002.

As shaft portion 2002 is moved in a first direction translationally (e.g., advanced toward blade 1815, such as through rotation force applied in a first rotation direction), force is exerted on connecting member 2015, which further exerts a force on blade 1815. The movement of shaft portion 2002 in the first direction accordingly causes blade 1815 to be deployed from fixation device 1800, such as into bone. Shaft portion 2002 can continue to be moved in the first direction to further deploy blade 1815 into bone, until blade 1815 is fully deployed.

As shaft portion 2002 is moved in a second direction translationally (e.g., receded away from blade 1815, such as through rotation force applied in a second rotation direction), force is exerted on connecting member 2015, which further exerts a force on blade 1815. The movement of shaft portion 2002 in the second direction accordingly causes blade 1815 to be retracted back into fixation device 1800, such as out of bone. Shaft portion 2002 can continue to be moved in the second direction to further retract blade 1815 from bone, until blade 1815 is fully retracted into fixation device 1800.

Figure 21:
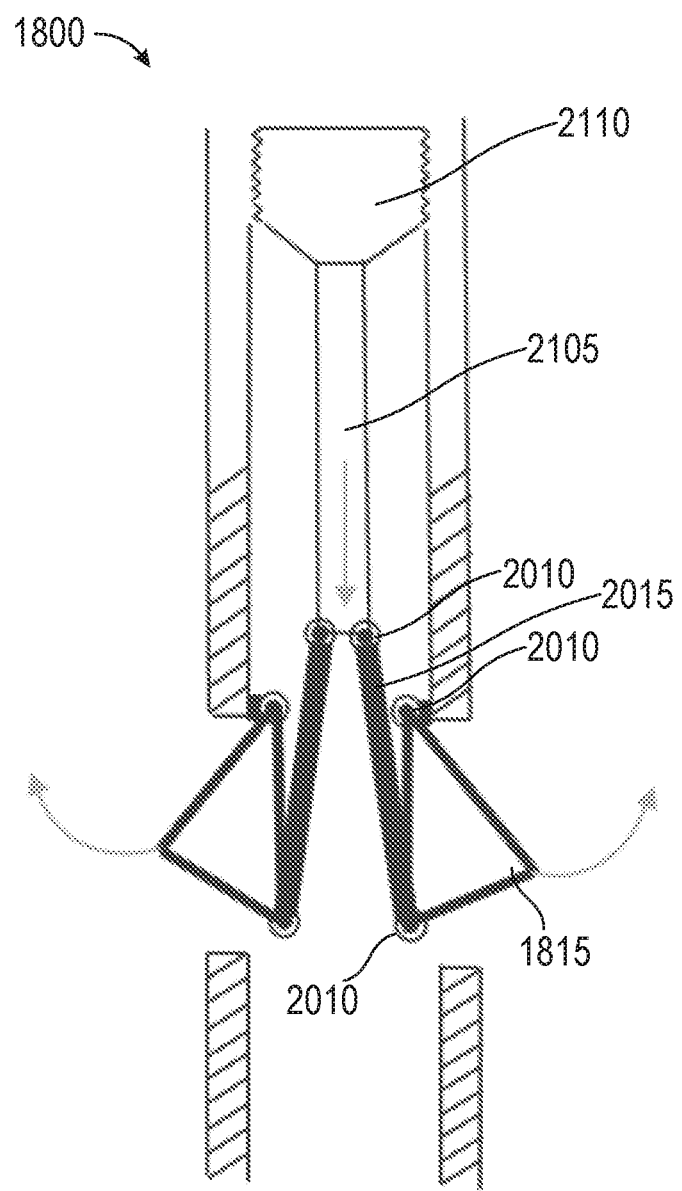
FIG. 21 illustrates another example activation mechanism of a fixation device, according to an embodiment.

FIG. 21 illustrates another example activation mechanism of fixation device 1800. The activation mechanism of FIG. 21 is similar to that of FIG. 20. However, instead of a shaft portion 2002, the activation mechanism includes a coupling member 2105 (e.g., a bar). As shown, in certain embodiments, the coupling member 2105 is not threaded. The coupling member 2105 is hingedly coupled to one or more blades 1815, each blade 1815 being directly coupled (not shown) or coupled via one or more connecting members 2015. The activation mechanism further includes a threaded cap 2110. The threaded cap 2110 includes threads, and in certain embodiments, an inner wall of the fixation device 1800 includes complementary threads to that of threaded cap 2110. In particular, interaction of the complementary threads and threads of threaded cap 2110 allow for threaded cap 2110 to be moved by rotational force (e.g., using an activation instrument), while retaining position after being moved.

In certain aspects, threaded cap 2110 is separate from coupling member 2105, but is configured to contact coupling member 2105 so as to apply force to move coupling member 2105 in a similar fashion as discussed with respect to shaft portion 2002. For example, threaded cap 2110 is configured to abut coupling member 2105. Such abutment allows threaded member 2105 to apply force in at least one direction to coupling member 2105.

In certain aspects, threaded cap 2110 is coupled to coupling member 2105 such that they are rotationally decoupled, but translationally coupled, such that as threaded cap 2110 is rotated, coupling member 2105 does not rotate, but as threaded cap 2110 is moved translationally (e.g., up and down) coupling member 2105 also moves accordingly. In one example, a portion of threaded cap 2110 is configured to surround coupling member 2105. Further coupling member 2105 may include a portion with a smaller circumference than other portions of coupling member 2105 surrounding said portion, thereby forming a notch around the circumference of coupling member 2105. The threaded cap 2110 accordingly may include a portion that extends into the notch, and that can rotate freely around the notch. In certain aspects, bearings may be used to facilitate such rotation. As the threaded cap 2110 is move translationally, the portion that extends into the notch may contact the portions of coupling member 2105 with a larger circumference surrounding the notch, and accordingly, force is applied to the coupling member 2105 to move it translationally in at least two directions.

For example, as threaded cap 2110 is moved in a first direction translationally (e.g., advanced toward blade 1815, such as through rotation in a first rotation direction), force is exerted on coupling member is, which exerts a force on connecting member 2015, which further exerts a force on blade 1815. The movement of threaded cap 2110 in the first direction accordingly causes blade 1815 to be deployed from fixation device 1800, such as into bone. Threaded cap 2110 can continue to be moved in the first direction to further deploy blade 1815 into bone, until blade 1815 is fully deployed.

As threaded cap 2110 is moved in a second direction translationally (e.g., receded away from blade 1815, such as through rotation force applied in a second rotation direction), force is exerted on coupling member 2105, which exerts a force on connecting member 2015, which further exerts a force on blade 1815. The movement of threaded cap 2110 in the second direction accordingly causes blade 1815 to be retracted back into fixation device 1800, such as out of bone. Threaded cap 2110 can continue to be moved in the second direction to further retract blade 1815 from bone, until blade 1815 is fully retracted into fixation device 1800.

One benefit of the activation mechanism of FIG. 21 is that the rotational force applied to threaded cap 2110 is not applied to coupling member 2105. This helps prevent deformation of coupling member 2105, and prevent such rotational force being applied to connecting member 2015 and even blade 1815, which could cause unwanted strain and/or deformation.

The use of a fixation device comprising one or more blades as discussed as part of a DHS system is further described with respect to FIGS. 22-27.

Figure 22:
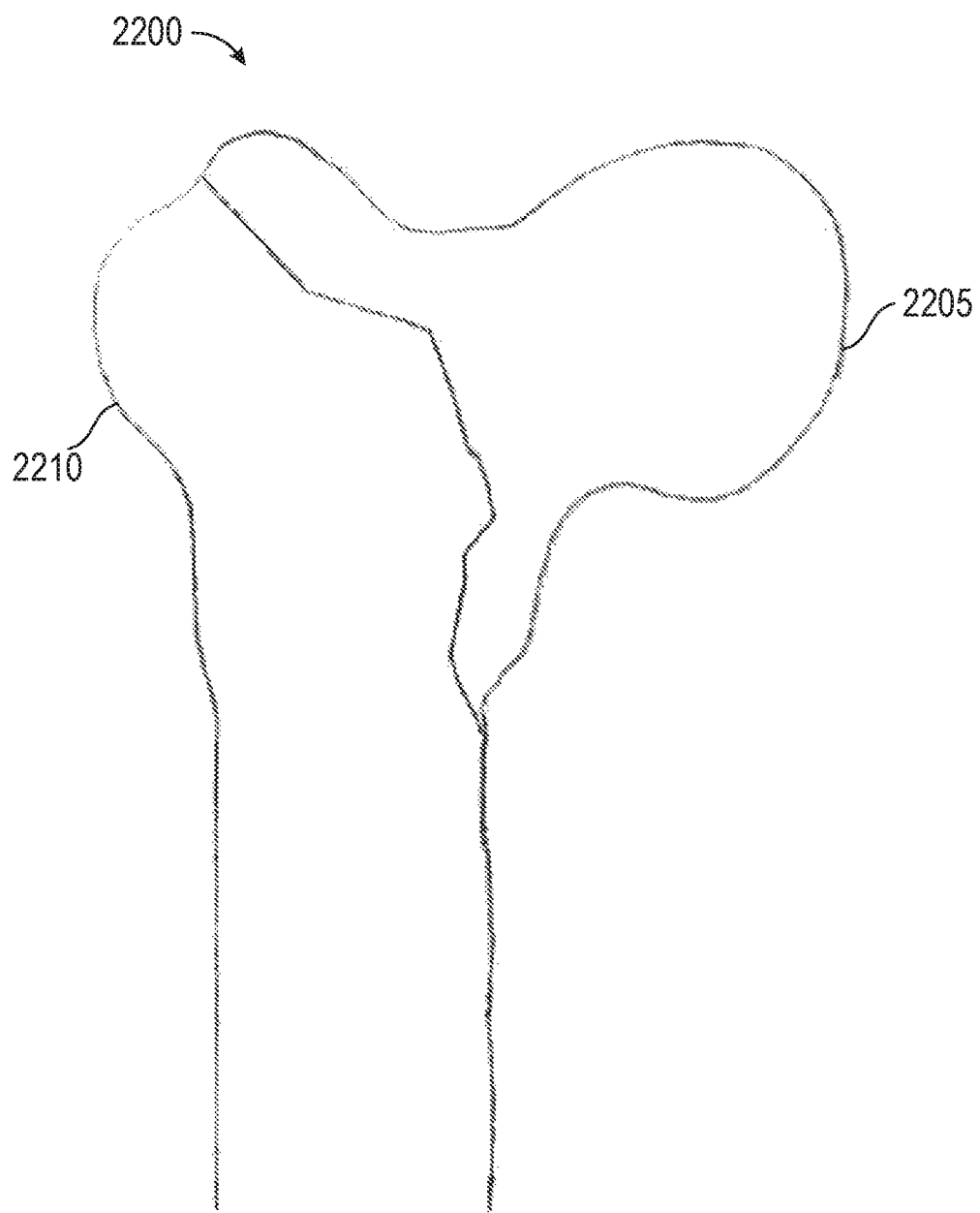
FIGS. 22-27 illustrate various stages of implantation of a DHS system comprising a fixation device having one or more blades into a femur, according to an embodiment.
Figure 23:
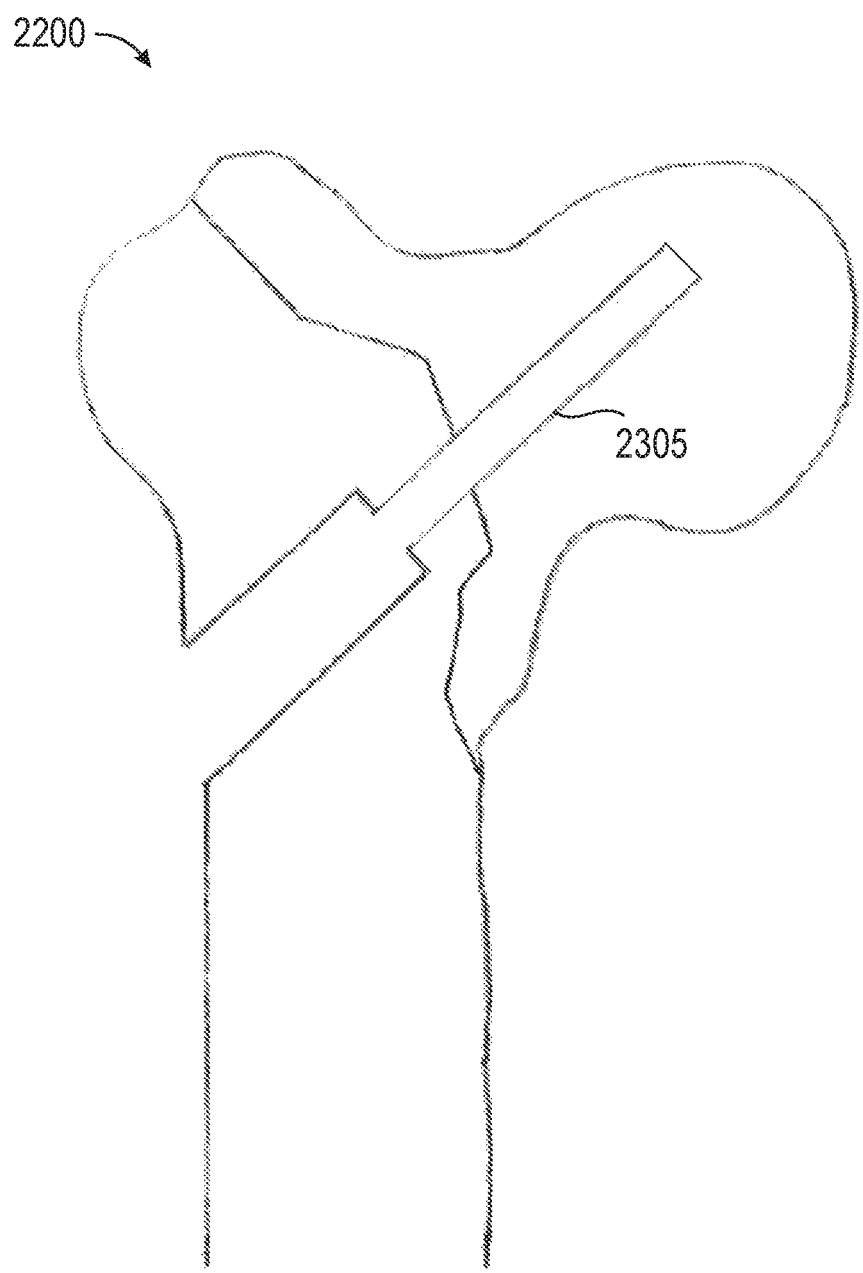

FIG. 22 illustrates a femur 2200 comprising a femoral head 2205 and a femoral neck 2210 that is to be implanted with a DHS system. In order for the DHS system to be implanted, a hole may be drilled through the femoral head 2205 and the femoral neck 2210. In certain aspects, the hole drilled may have different circumferences at different portions, such as a smaller circumference deeper in the hole to receive threading of a lag screw, and a larger circumference shallower in the hole to accommodate a barrel of a plate. FIG. 23 illustrates an example hole 2305 drilled into the femur 2200.

Figure 24:
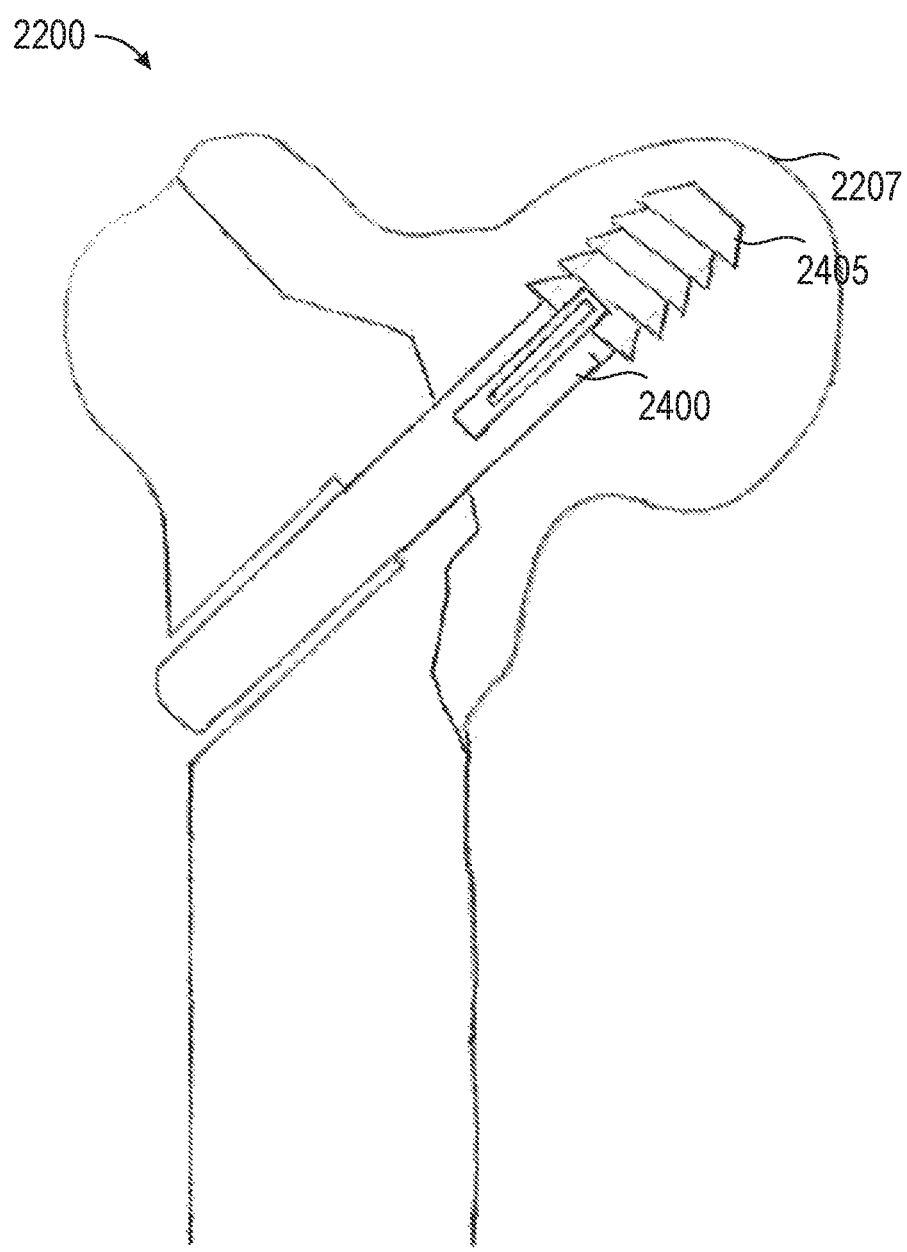

After the hole 2305 is drilled into femur 2200, a lag screw 2400 is inserted into the hole 2305 and accordingly the femur 2200 as shown in FIG. 24. The lag screw 2400 is an example fixation device (e.g., fixation device 1800) comprising one or more deployable blades as discussed. For example, the lag screw 2400 is inserted into the patient's proximal femur 2200 from the lateral side, through the femoral neck 2210 to a position where ideally the head 2405 of the lag screw 2400 sits an optimal distance from the cortex 2207 of the femoral head 2205.

Figure 25:
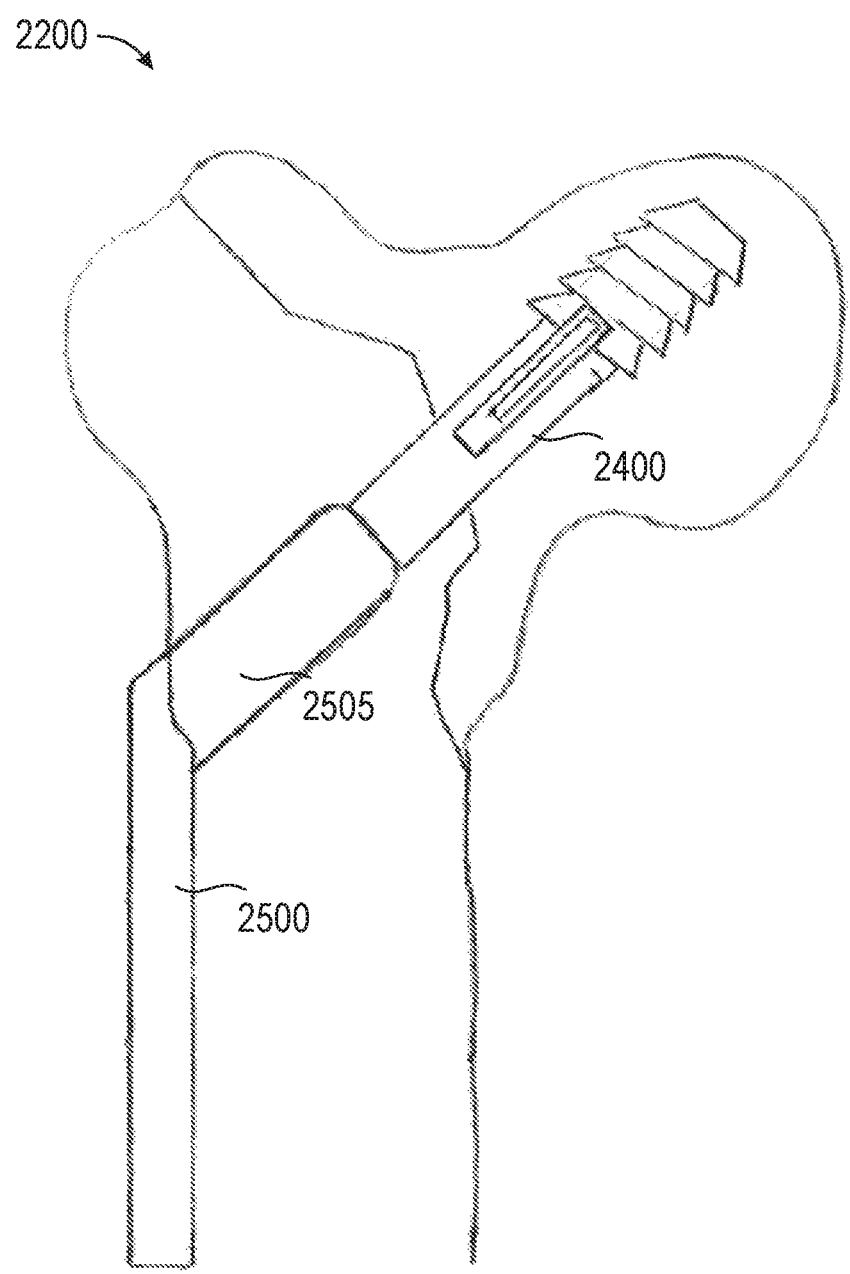
Figure 26:
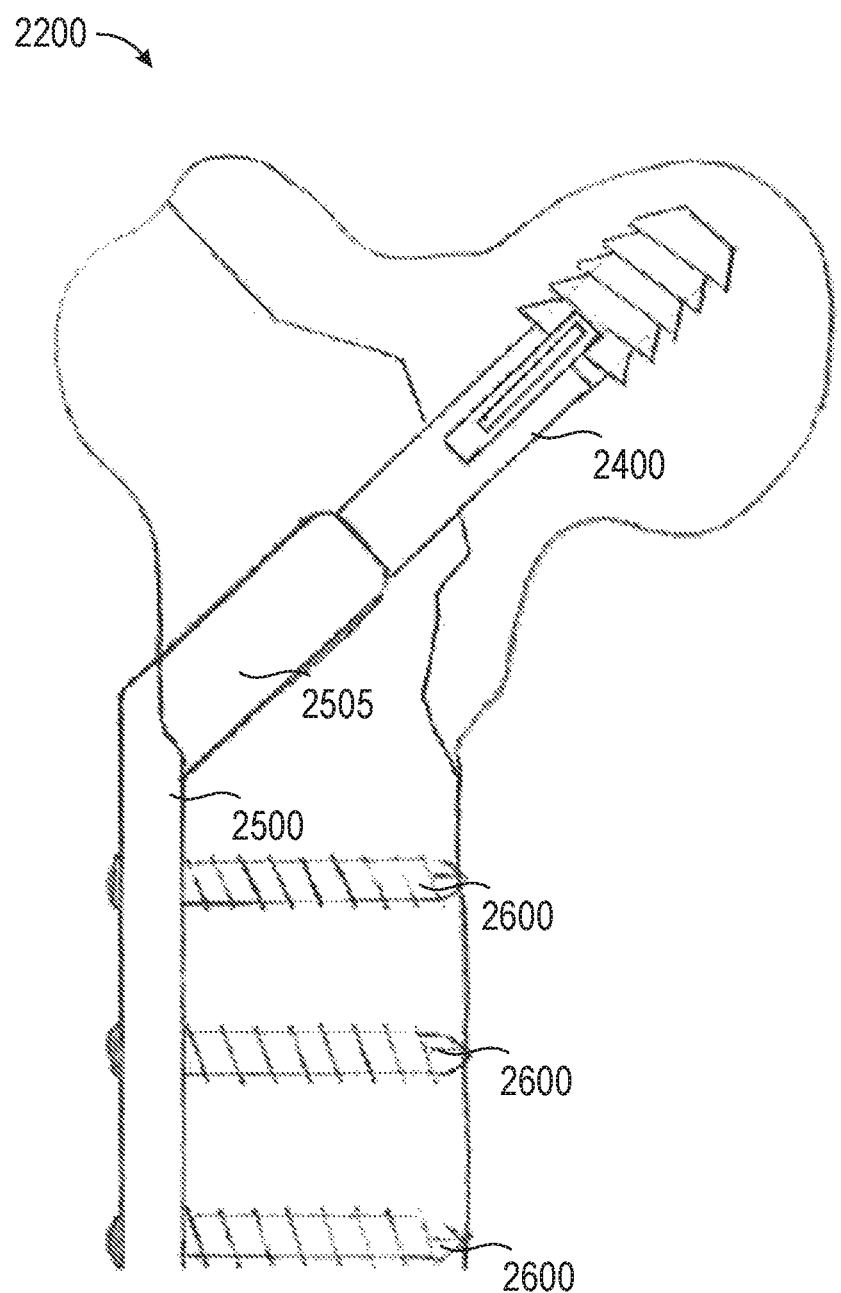

Once the lag screw 2400 is in place, a plate 2500 is applied to the femur 2200, sliding a barrel 2505 of the plate 2500 over the end of the lag screw 2400 as shown in FIG. 25. The plate 2500 is then fixed to the lateral side of the femur 2200 with cortical bone screws 2600 as shown in FIG. 26. In certain embodiments, at this stage, a locking screw (not shown) is applied in the barrel 2505, which prevents the lag screw 2400 from sliding in the plate barrel 2505. However, such a locking screw may not be used as the sliding function allows compressive collapse during loading, creating dynamic stresses at the fracture interface which in turn facilitates primary bone healing.

Figure 27:
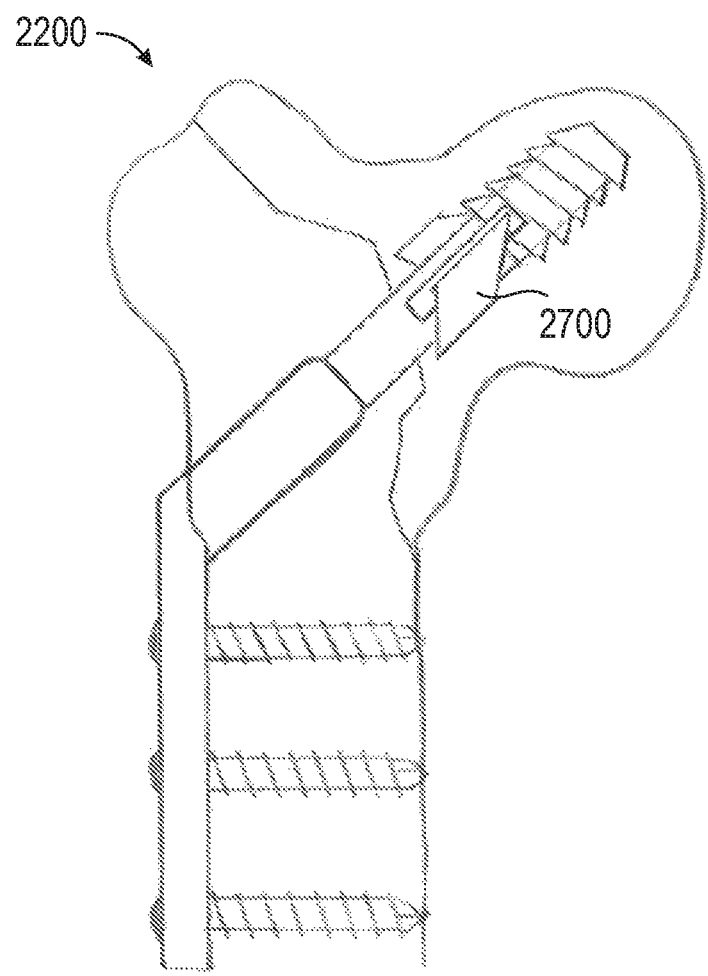

At this point an activation mechanism inside the lag screw 2400 is engaged whereby blades 2700 that are housed in the lag screw 2400 are deployed and cut into the surrounding bone as shown in FIG. 27 as discussed. Accordingly, lag screw 2400 has improved purchase in femur 2200, thereby preventing cut-out as discussed.

Figure 28:
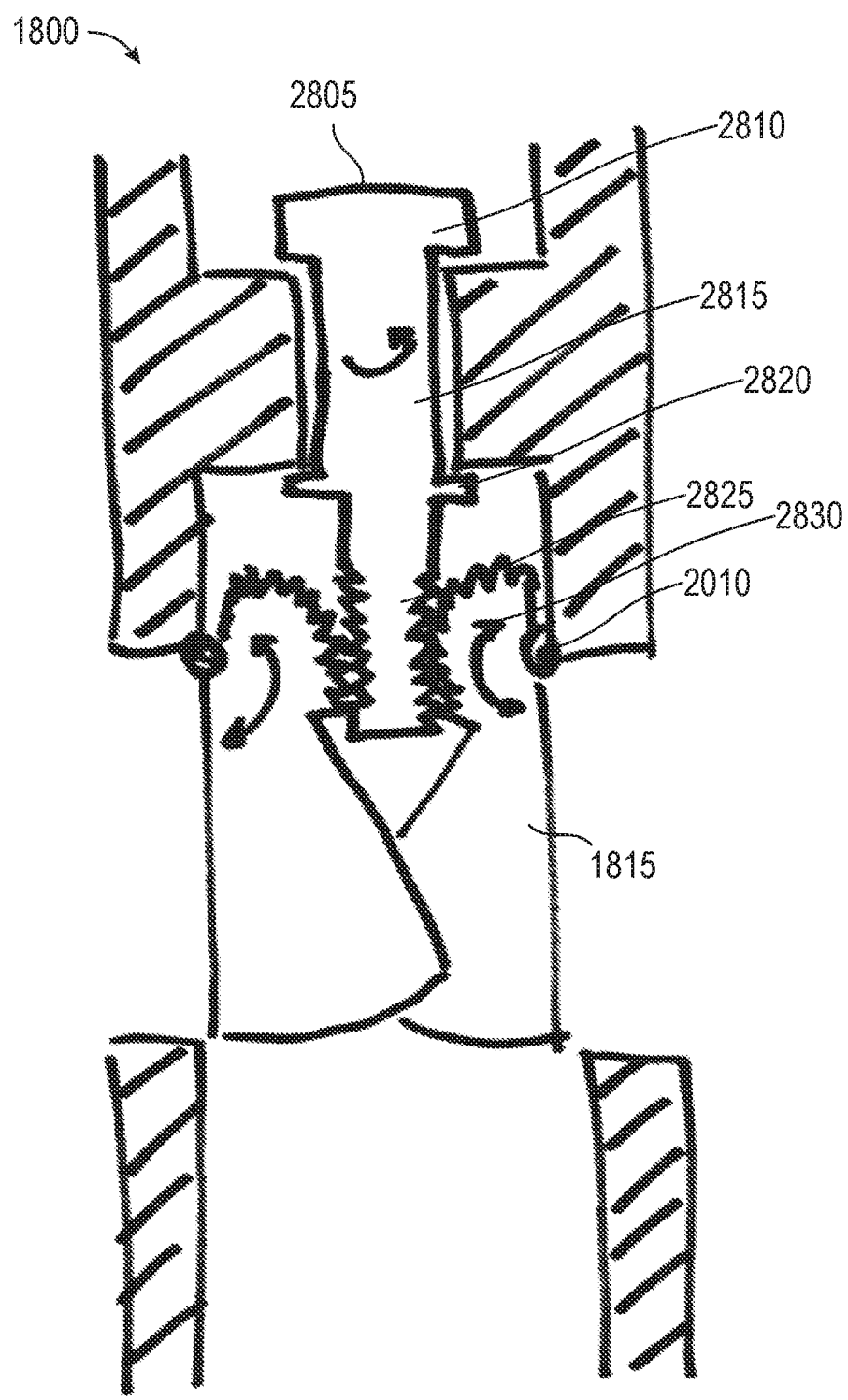
FIG. 28 illustrates another example activation mechanism of a fixation device, according to an embodiment.

FIG. 28 illustrates another example activation mechanism of fixation device 1800. The activation mechanism of FIG. 28 is similar to that of FIG. 20. However, the activation mechanism includes a coupling member referred to as a rotating element 2805 (e.g., shaft, bar, etc.). The rotating element 2805 includes areas 2810 and 2820 having a larger circumference, and a notch area 2815 having a smaller circumference, thereby forming a notch around the circumference of rotating element 2805. An inner-wall of fixation device 1800 includes a protrusion that is complementary to notch area 2815 and projects into notch area 2815 so as to restrict translational movement of rotating element 2805 while allowing rotational movement of rotating element 2805. An end of rotating element 2805 further includes a threaded area 2825.

As shown, one vertex or node of blade 1815 is coupled to a wall of fixation device 1800. For example, blade 1815 is hingedly coupled at a hinge 2010 to a (e.g., inner) wall of fixation device 1800, thereby allowing blade 1815 to rotate and deploy from inside fixation device 1800 to outside fixation device 1800 while remaining coupled to fixation device 1800. Further, blade 1815 includes a threaded portion 2830. The threaded portion 2830 includes complementary threads to threaded area 2825 and abuts threaded area 2825.

As rotating element 2805 is moved in a first direction rotationally (e.g., such as through rotation force applied in a first rotation direction by an activation instrument), threaded area 2825 rotates, thereby interacting with threaded portion 2830, which causes movement of blade 1815 about hinge 2010. The rotation of rotating element 2805 in the first direction accordingly causes blade 1815 to be deployed from fixation device 1800, such as into bone. Rotating element 2805 can continue to be moved in the first direction to further deploy blade 1815 into bone, until blade 1815 is fully deployed.

As rotating element 2805 is moved in a second direction rotationally (e.g., such as through rotation force applied in a second rotation direction by an activation instrument), threaded area 2825 rotates, thereby interacting with threaded portion 2830, which causes movement of blade 1815 about hinge 2010. The rotation of rotating element 2805 in the second direction accordingly causes blade 1815 to be retracted back into fixation device 1800, such as out of bone. Rotating element 2805 can continue to be moved in the second direction to further retract blade 1815 from bone, until blade 1815 is fully retracted into fixation device 1800.

One benefit of the activation mechanism of FIG. 28 is that no translational movement of rotating element 2805 is needed.

Figure 29:
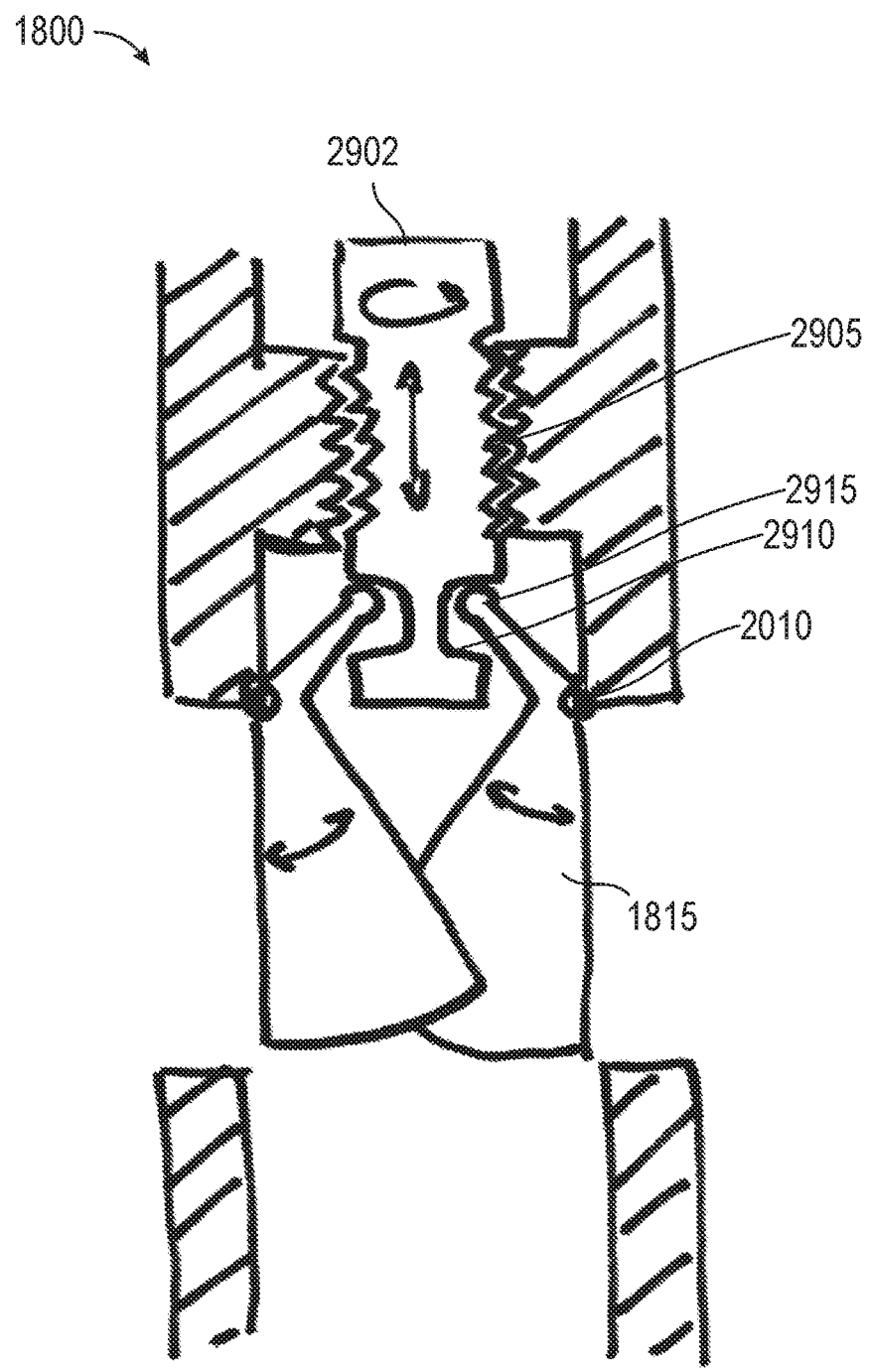
FIG. 29 illustrates another example activation mechanism of a fixation device, according to an embodiment.

FIG. 29 illustrates another example activation mechanism of fixation device 1800. The activation mechanism of FIG. 29 is similar to that of FIG. 20. The coupling member includes a shaft portion 2902 having a threaded region 2905. However, unlike shaft portion 2002 of FIG. 20, shaft portion 2902 is not coupled by a standard hinge to blade 1815. Instead, shaft portion 2902 includes a portion with a smaller circumference than other portions of shaft portion 2902 surrounding said portion, thereby forming a notch 2910 around the circumference of shaft portion 2902. The blade 1815 accordingly includes a lever 2915 that extends into the notch 2910, allowing shaft portion 2902 to rotate while not applying rotational force to blade 1815. As the shaft portion 2902 is moved translationally, the lever 2915 of blade 1815 that extends into the notch 2910 may contact the portions of shaft portion 2902 with a larger circumference surrounding the notch 2910, and accordingly, force is applied to the lever 2915 of blade 1815 causing movement of blade 1815.

As shown, one vertex or node of blade 1815 is coupled to a wall of fixation device 1800. For example, blade 1815 is hingedly coupled at a hinge 2010 to a (e.g., inner) wall of fixation device 1800, thereby allowing blade 1815 to rotate and deploy from inside fixation device 1800 to outside fixation device 1800 while remaining coupled to fixation device 1800.

For example, as shaft portion 2902 is moved in a first direction translationally (e.g., advanced toward blade 1815, such as through rotation in a first rotation direction), force is exerted on lever 2915, which causes movement of blade 1815 about hinge 2010. The movement of shaft portion 2902 in the first direction accordingly causes blade 1815 to be deployed from fixation device 1800, such as into bone. Shaft portion 2902 can continue to be moved in the first direction to further deploy blade 1815 into bone, until blade 1815 is fully deployed.

As shaft portion 2902 is moved in a second direction translationally (e.g., receded away from blade 1815, such as through rotation force applied in a second rotation direction), force is exerted on lever 2915, which causes movement of blade 1815 about hinge 2010. The movement of shaft portion 2902 in the second direction accordingly causes blade 1815 to be retracted back into fixation device 1800, such as out of bone. Shaft portion 2902 can continue to be moved in the second direction to further retract blade 1815 from bone, until blade 1815 is fully retracted into fixation device 1800.

One benefit of the activation mechanism of FIG. 29 is that the rotational force applied to shaft portion 2902 is not applied to blade 1815. This helps prevent such rotational force being applied to blade 1815, which could cause unwanted strain and/or deformation.

It should be noted that though several embodiments illustrate blades as substantially parallel to the longitudinal axis of the fixation device, other orientations are possible, such as to accommodate to different loading scenarios, e.g. due to different fracture types.

In certain embodiments, where a fixation device has multiple blades, the blades may be deployable separately, such as to accommodate different fracture situations, surgeon need, etc. For example, a fixation device 1800 may include multiple blades 1815 that are individually deployable (e.g., between a first position such as a retracted position, and a second position such as a deployed position, or any positions in between).

Figure 30:
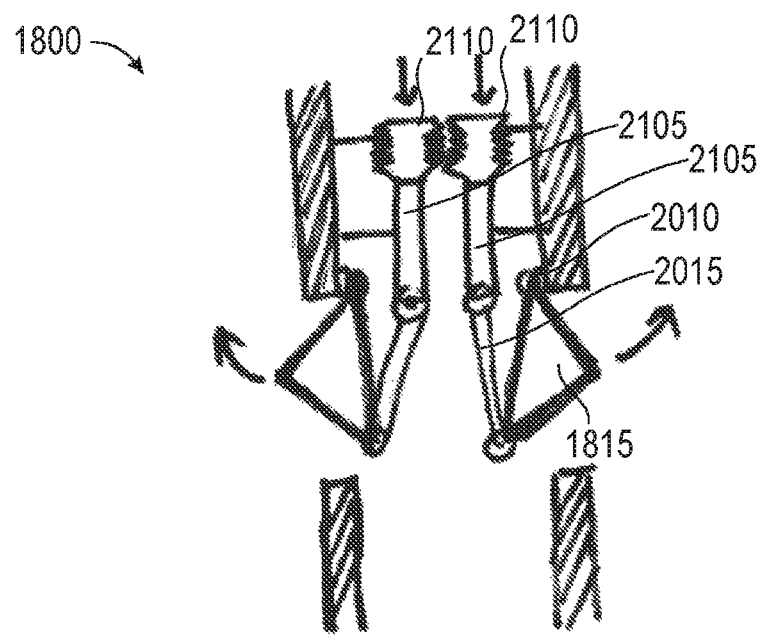
FIG. 30 illustrates another example activation mechanism of a fixation device, according to an embodiment.

FIG. 30 illustrates another example activation mechanism of fixation device 1800. FIG. 30 is similar to the activation mechanism of FIG. 21. However, instead of a single threaded cap 2110 and a single coupling member 2105, the activation mechanism of FIG. 21 includes multiple threaded caps 2110, each configured to exert force as discussed on one of multiple coupling members 2105. Each coupling member 2105 may be coupled (e.g., hingedly) to a separate connecting member 2015, which further is coupled (e.g., hingedly) to a separate blade 1815. Accordingly, each threaded cap 2110 can be separately moved to thereby separately deploy different blades 1815, similar to as discussed with respect to FIG. 21.

Figure 31:
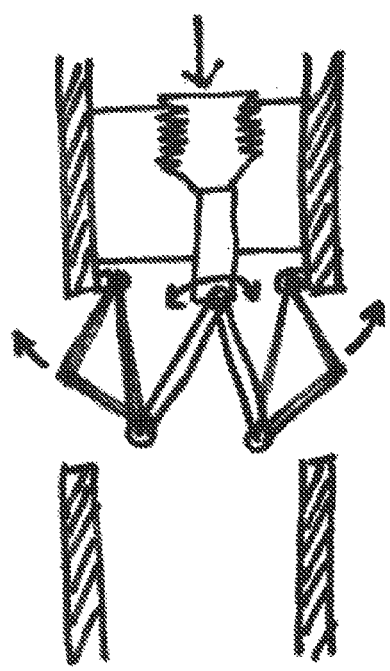
FIG. 31 illustrates another example activation mechanism of a fixation device, according to an embodiment.

FIG. 31 illustrates another example activation mechanism configured to have blades that are separately deployable.

Figure 32:
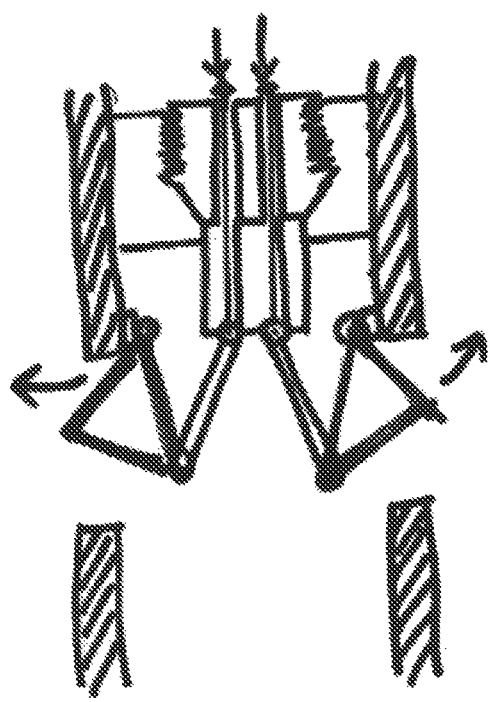
FIG. 32 illustrates another example activation mechanism of a fixation device, according to an embodiment.

FIG. 32 illustrates another example activation mechanism configured to have blades that are separately deployable.

In certain embodiments, the fixation device (e.g., as shown in FIGS. 8A-8D) comprises one or more spike arms as puncturing elements. In certain embodiments, spike arms are sharp limbs of the fixation device that can expand from within the fixation device casing to penetrate the host bone. In certain embodiments, there is a 'slot pin' on one end of the spike arm that comes in contact with slots of a gear wheel such that rotation of the gear wheel is converted into a translation of the spike arm. In certain embodiments, the fixation device includes a gear wheel. In certain embodiments the gear wheel includes a slot to house the pin of each spike arm. In certain embodiments the gear wheel rotates on its own central 'rotation' pin that is in contact with the fixation device casing. In certain embodiments, the gear wheel is rotated by means of a hole compatible with a standard screw driver. In certain embodiments, the fixation device includes a casing. In certain embodiments, the casing houses the spike arms, providing boundary conditions such that each arm undergoes unidirectional translation upon rotation of the gear wheel. In certain embodiments, the casing also houses the pin of the gear wheel, providing boundary conditions such that only rotation of the gear wheel is achievable.

In certain embodiments, the fixation device comprises an expansion device (e.g., as shown in FIGS. 7A-7B and FIGS. 6A-6G). For example, in certain embodiments, the fixation device includes expandable elements that when deployed expand the size of the non-deployed fixation device and compress the bone. In certain embodiments, sharp features can be included on the expandable elements for additional bone fixation. In certain embodiments, these expandable elements can be retracted when it is needed to remove the fixation mechanism. In certain embodiments, the deployment of the expandable elements can be activated by various mechanism such as by exerting pressure, applying a torque or other, in a way that can be manual, by use of a separate activation instrument (pin, internal screw, etc.) or other. The expandable elements may create a press-fit fixation of the fixation device to the bone. Further, traditional bone screws have the design restriction that the friction generated by the screw thread during device insertion into the bone must be low for ease of insertion. In contrast, the expandable elements can be optimized for ease of insertion (low friction in insertion direction).

In certain embodiments, a fixation device comprising an expansion device includes expandable elements comprising outer flaps. In certain embodiments, the outer flaps apply a compressive force to the host bone. In certain embodiments, the outer flaps include legs of the flaps that are housed within an inner cylindrical cavity of the fixation device to receive an insertion pin. The outer flaps may contain porous structure and/or barbs. In certain embodiments, the fixation device includes an inner cylindrical cavity that houses the legs of the outer flaps such that they are contained and prevented from dislocating from the fixation device. In certain embodiments, the fixation device includes an activation mechanism for activating (deploying or retracting) the expandable elements such as by exerting pressure, applying a torque or other, in a way that can be manual, by use of a separate activation instrument (insertion pin, internal screw, etc.) or other. In certain embodiments, the activation mechanism includes one or more gear wheels as shown in FIGS. 8A-D. In certain embodiments, the fixation device includes barbs comprising unidirectional spikes attached to the outer flaps. The barbs may be positioned and angled so that they allow easy insertion of the fixation device into a pre-made cavity in the bone, but resist pullout of the fixation device and part from the bone when engaged (they provide initial fixation of the part).

In certain embodiments, the fixation device comprises a combination puncturing and expansion device. For example, the fixation device includes both puncturing elements and expandable elements, one or more of which may include porous structures. In certain aspects, the fixation device includes outer flaps configured to apply a radial piercing and compressive force to the host bone. In certain embodiments, legs of the flaps are housed within an inner cylindrical cavity of the fixation device to receive an insertion pin. The outer flaps may contain porous structure and/or barbs. In certain embodiments, the fixation device includes an inner cylindrical cavity that houses the legs of the outer flaps such that they are contained and prevented from dislocating from the fixation device. In certain embodiments, the fixation device includes an activation mechanism for activating (deploying or retracting) the expandable elements such as by exerting pressure, applying a torque or other, in a way that can be manual, by use of a separate activation instrument (insertion pin, internal screw, etc.) or other. In certain embodiments, the activation mechanism includes one or more gear wheels as shown in FIGS. 8A-D. In certain elements, legs of puncturing elements are housed within the inner cylindrical cavity along with the legs of the outer flaps.

Figure 9:
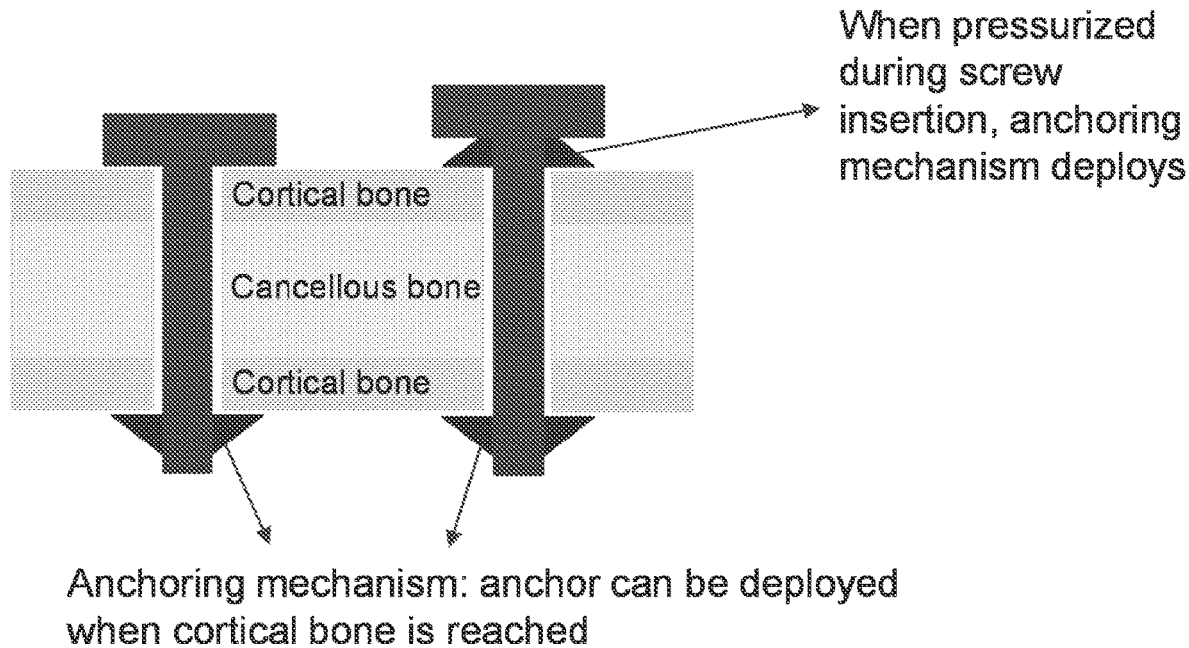
FIG. 9 provides an example of a fixation device with anchoring elements.

In certain embodiments, the fixation device (e.g., as shown in FIG. 9) comprises an anchoring device. In certain embodiments, the fixation device includes one or more anchoring elements that when deployed anchor behind cortical bone. In certain embodiments, these anchoring elements can be retracted when it is needed to remove the fixation device. The deployment of the anchoring elements can be activated by various mechanisms such as by exerting pressure, applying a torque or other, in a way that can be manual, by use of a separate activation instrument (pin, internal screw, etc.) or other. One advantage of such an anchoring technique is improved purchase in high quality bone.

In certain embodiments, a fixation device comprising an anchoring device comprises a plug made either solid or from porous structure that protrudes into a premade bone cavity (e.g., can be attached to an essential part of an anatomy specific). The plug further includes a plug cavity that houses the anchoring elements and an activation mechanism comprising an anchor deployment mechanism. In certain embodiments, the anchoring elements comprise sharp entities that protrude laterally from the tip of the plug into the host bone to create a hook-like feature. In certain embodiments the anchor deployment mechanism comprises a push-pin that applies pressure to a region of the anchoring elements such that they engage in the host bone. In certain embodiments the anchor deployment mechanism comprises a threaded bolt such that when inserted into a threaded plug cavity and torque is applied, the anchoring elements are forced to protrude laterally and engage in the host bone. In certain embodiments the anchor deployment mechanism comprises a mechanism underneath a screw head that gets squeezed between the screw head and bone when the screw head approaches the bone during screw insertion. The pressure on this mechanism may then activate the anchoring elements at the bottom of the screw.

Certain embodiments provide promotion of bone remodeling. For certain embodiments provide flexible fixation devices (e.g., as shown in FIGS. 11-14). According to Wolff's law, bone will adapt to the loads under which it is placed. When loading of the bone increased, the bone will remodel and become stronger. When loading decreases, the bone will become weaker because continued bone remodeling is not stimulated. Accordingly, certain embodiments enable continued bone remodeling of the bone adjacent to the fixation device, by improved load sharing between the bone and the fixation device. In certain embodiments, the fixation device is entirely or partially flexible, allowing load to be applied to the adjacent bone.

In certain embodiments, the flexible part of the fixation device can be made rigid (using a bypass or other hardening mechanism) for insertion of the fixation device into the bone. Once the fixation device is seated, the hardening mechanism may be deactivated.

Certain embodiments provide a flexible fixation screw. The screw includes threads (e.g., to gain initial purchase in the host bone) and a screw driver hole (e.g., to allow insertion of the screw a hole in the screw compatible with a standard screw driver may be provided). One or more flexible structures may be located anywhere on the screw body. In certain embodiments, a flexible structure comprises a mesh structure of struts offset from one another such that they are able to move relative to each other (flexible mode). After a certain amount of movement the struts may come in contact with each other causing the mesh structure to become rigid (rigid mode).

Certain embodiments provide post-processing techniques. The manufacturing process is important in determining the overall performance of fixation devices (e.g., fixation screws). Namely, cutting of the threads to achieve geometrical accuracy and 'sharpness' is an important step that can feasibly be achieved by CNC machining.

During traditional manufacturing of a screw the solid raw material is loaded in the CNC machine and is cut with specific tools to obtain particular screw parameters. The material loaded in the CNC machine is always a solid piece of metal, meaning the resulting screw is solid.

In certain embodiments, instead of using a solid material in the CNC machine, a piece of material is provided that has been 3D printed such that, once cut to shape, the fixation screw would have a porous layer with solid threads and core.

In certain embodiments, a material used by a CNC machine to cut a screw from comprises a full cylinder (slug). A full cylinder may comprise a solid cylindrical shell, with solid cross-section at the tip and head regions. In the region where thread cutting will take place, there is a porous tube within the cylinder. Once the cylinder is cut to shape the porous structure is exposed so that there is a porous layer on each helical thread.

The cylinders can take various forms to achieve different orientations of the porous structure and allow for other features such as cannulation holes.

In certain embodiments, a material used by a CNC machine to cut a screw from comprises a grooved cylinder. A grooved cylinder comprises porous structure that is exposed before CNC machining. A helical groove circumvents the length of the thread region exposing the porous structure. The CNC machine cuts away material at the head, tip and the solid material between the helical grooves to shape the solid threads. This avoids the necessity of CNC machining the potentially brittle porous structure and achieves high dimensional accuracy of the solid regions of the screw.

Other potential post-processing techniques may include polishing, grinding, reaming, blasting and anodizing. All of these can contribute to the dimensional accuracy of the fixation device and as such its effectiveness in providing stable fixation.

Figure 10A:
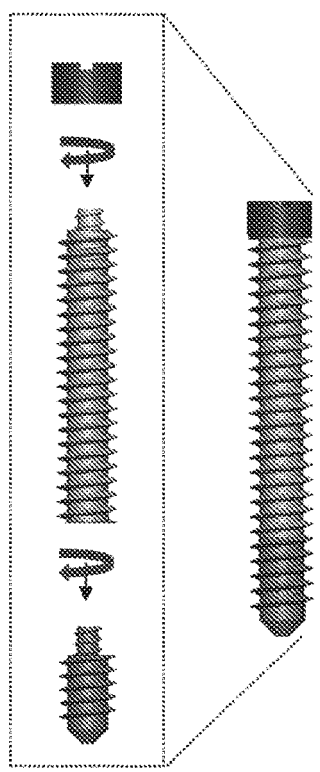
FIGS. 10A-10B provide examples of a fixation device with assembly mechanisms.
Figure 10B:
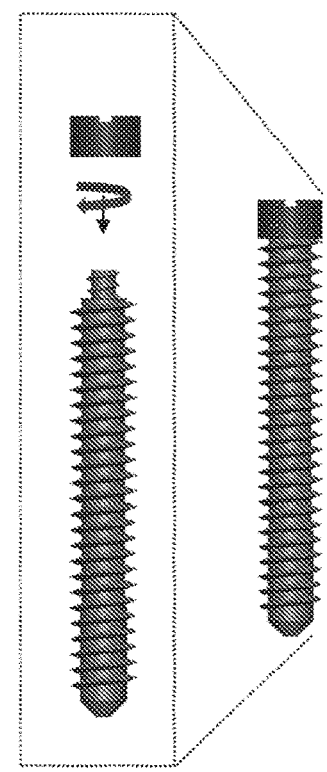
Figure 11:
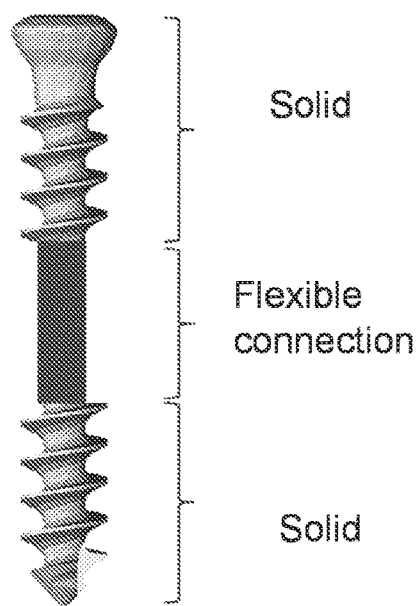
FIGS. 11-14 provide examples of a fixation device with flexible structure.
Figure 12:
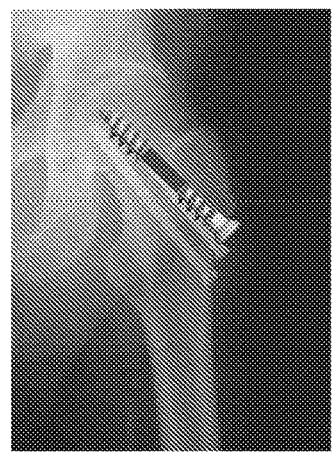
Figure 13:
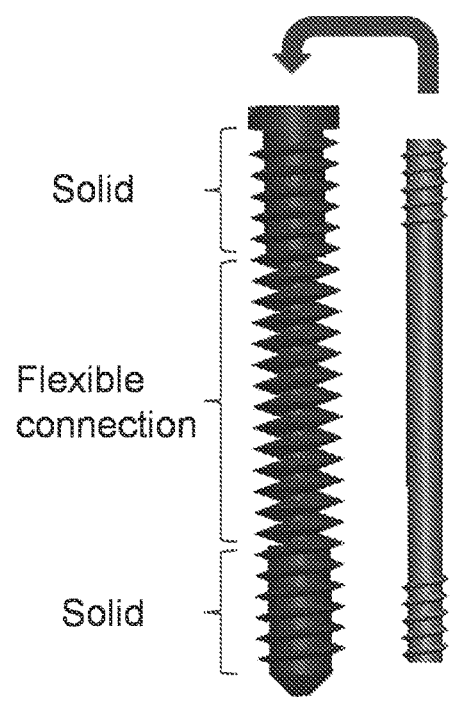
Figure 14:
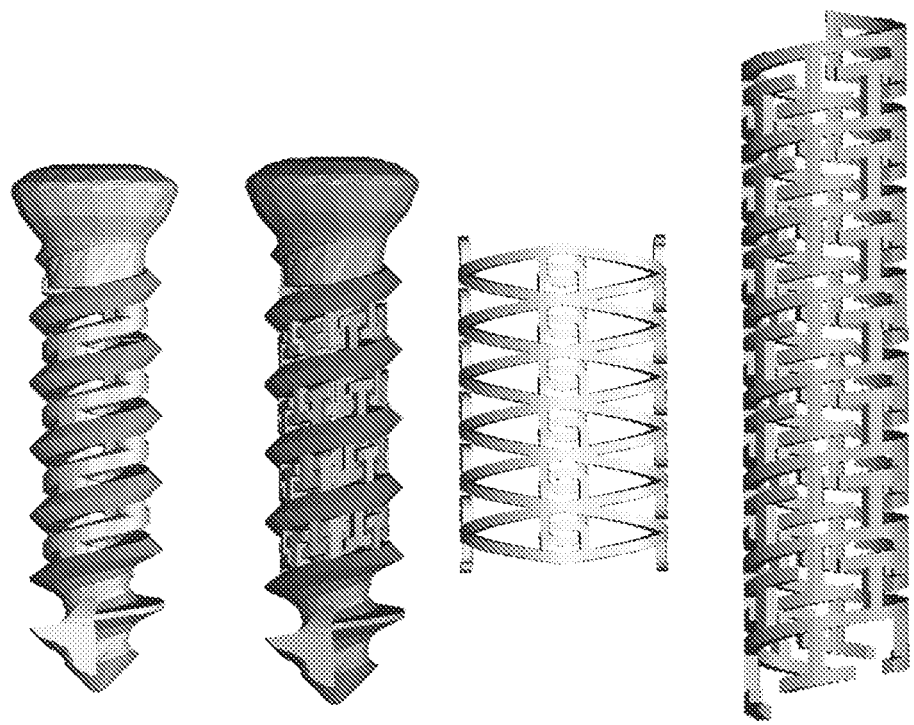

In certain embodiments, a fixation device (e.g., as shown in FIGS. 10A-10B) includes one or more assembly mechanisms, which may improve ease of insertion of the fixation device in bone. For example, a fixation device such as a screw can be built up out of separate smaller parts, and the assembly mechanisms may allow the parts to be assembled. Assembly mechanisms may include one or more of screw-within-a-screw, click-on features, etc. One of many possible examples is a screw that includes two parts: a shaft and a head. The head could be assembled onto the shaft intraoperatively, after prior insertion of the shaft. A fixation device including one or more assembly mechanisms may provide intraoperative freedom to decide on the shape of the screws such as the ratio of porous and solid parts.

In one example, the head of a 2-part screw can be assembled onto the shaft: During the use of patient specific guiding instruments which serve to predrill screw holes for implant fixation, the surgeon is required to iteratively predrill a screw holes, take off the guide, insert a screw and reposition the guide. By having screws that allow the heads to be added later, the surgeon could already insert the screw shafts without the need for taking off the guide. In this way the number of times that the surgeon is required to take off the guide is reduced significantly. This improves the ease of use and shortens the surgery duration which has both economical and patient health-related benefits.

In certain embodiments, embodiments described herein, such as of fixation devices, may be manufactured using an additive manufacturing AM process.

AM processes are a material-addition approach to building parts, typically starting from a base material in liquid, solid sheet or powder form and consolidating the added material locally, in layer-by-layer fashion. Since the emergence of the first AM processes in the early 1990's, AM processes have been used as an alternative to conventional material-removal techniques such as milling, cutting or drilling or molding techniques, such as injection molding or extrusion molding, and have been shown to be especially effective in producing complex parts in a relatively short time, without dedicated tools such as molds or dies.

Among the best-known AM techniques are stereolithography (SLA), 3D-printing (3D-P), Selective Laser Sintering (SLS), Selective Heat Sintering (SHS), Selective Laser Melting (SLM), Direct Metal Laser Sintering (DMLS), Laser Beam Melting (LBM), and Electron Beam Melting (EBM). The techniques vary according to the tools used for consolidating the layers of a part, and according to materials that can be used in the techniques.

The systems and methods described herein may be performed using various additive manufacturing and/or three-dimensional (3D) printing systems and techniques. Typically, additive manufacturing techniques start from a digital representation (e.g., CAD file, such as STL, DWG, DXF, etc., mesh based model, voxel based model, etc.) of the 3D object to be formed. Generally, the digital representation is divided into a series of cross-sectional layers (e.g., perpendicularly to the Z-direction, meaning parallel to a build platform), or "slices," which are overlaid to form the object as a whole. The layers represent the 3D object, and may be generated using additive manufacturing modeling software executed by a computing device. For example, the software may include computer aided design and manufacturing (CAD/CAM) software. Information about the cross-sectional layers of the 3D object may be stored as cross-sectional data. An additive manufacturing (e.g., 3D printing) machine or system utilizes the cross-sectional data for the purpose of building the 3D object on a layer by layer basis. Accordingly, additive manufacturing allows for fabrication of 3D objects directly from computer generated data of the objects, such as computer aided design (CAD) files or STL files. Additive manufacturing provides the ability to quickly manufacture both simple and complex parts without tooling and without the need for assembly of different parts.

Additive manufacturing processes generally include providing energy from an energy source (e.g., a laser, an electron beam, etc.) to solidify (e.g., polymerize) layers of building material (e.g., plastic, metal, etc.). For example, the additive manufacturing machine may selectively apply energy from an energy source to (e.g., scan) the building material based on a job file. The job file may include information regarding slices of a digital representation of an object or objects to be built using an additive manufacturing process. For example, 3D objects represented by CAD files may be arranged in a virtual build volume corresponding to the build volume of an additive manufacturing device. Optionally, support structures may be added to the 3D objects in the virtual build volume (e.g., to improve build quality, heat dissipation, reduce deformation, etc.) The resulting 3D objects may be divided into layers or slices, as discussed. The job file, accordingly, may include slices (e.g., a stack of slices) of the 3D objects, and parameters of the additive manufacturing machine for building the 3D objects.

For example, for each slice, the job file may include information regarding a scanning pattern for the energy source to apply energy to (e.g., laser to scan, electron beam to scan, etc.) the physical layer of building material corresponding to that slice. It should be noted that as discussed herein, the terms slice and layer may be used interchangeably. The scanning pattern may include one or more vectors that each indicates a spatial position to apply the energy to the layer of building material and a direction to apply the energy to the building material (e.g., a direction to move the laser beam, electron beam, or other energy source over the building material while scanning).

An additive manufacturing machine builds an object on a layer by layer basis by applying energy to (e.g., scanning) the layers of building material according to the scanning pattern for each individual layer as indicated in a job file. For example, the additive manufacturing machine may scan a first layer of physical building material corresponding to a first slice of a digital representation of an object according to the scanning pattern for the first slice. The additive manufacturing machine may then scan a second layer of building material corresponding to a second slice adjacent to the first slice according to the scanning pattern for the second slice. The additive manufacturing machine continues scanning layers of building material corresponding to all the slices in the job file, until the layer corresponding to the last slice is scanned.

Figure 15:
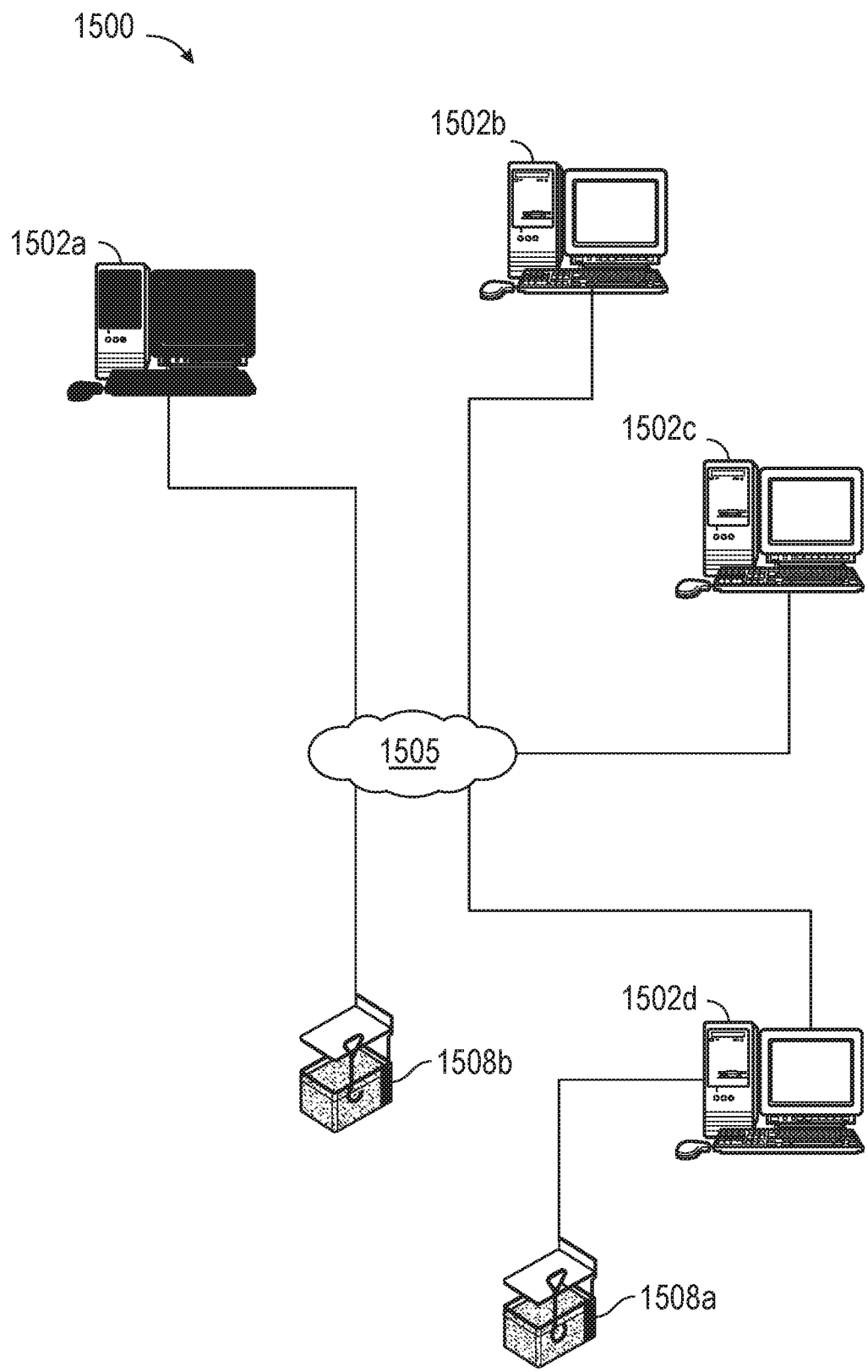
FIG. 15 is an example of a system for designing and manufacturing 3D objects.

Embodiments of the invention may be practiced within a system for designing and manufacturing 3D objects. Turning to FIG. 15, an example of a computer environment suitable for the implementation of 3D object design and manufacturing is shown. The environment includes a system 1500. The system 1500 includes one or more computers 1502a-1502d, which can be, for example, any workstation, server, or other computing device capable of processing information. In some aspects, each of the computers 1502a-1502d can be connected, by any suitable communications technology (e.g., an internet protocol), to a network 1505 (e.g., the Internet). Accordingly, the computers 1502a-1502d may transmit and receive information (e.g., software, digital representations of 3-D objects, commands or instructions to operate an additive manufacturing device, etc.) between each other via the network 1505.

The system 1500 further includes one or more additive manufacturing devices (e.g., 3-D printers) 1508a-1508b. As shown the additive manufacturing device 1508a is directly connected to a computer 1502d (and through computer 1502d connected to computers 1502a-1502c via the network 1505) and additive manufacturing device 1508b is connected to the computers 1502a-1502d via the network 1505. Accordingly, one of skill in the art will understand that an additive manufacturing device 1508 may be directly connected to a computer 1502, connected to a computer 1502 via a network 1505, and/or connected to a computer 1502 via another computer 1502 and the network 1505.

It should be noted that though the system 1500 is described with respect to a network and one or more computers, the techniques described herein also apply to a single computer 1502, which may be directly connected to an additive manufacturing device 1508. Any of the computers 1502a-1502d may be configured to function as the computing device described with respect to FIGS. 1-14. Further, any of the computers 1502a-1502d may be configured to perform the operations described herein.

Figure 16:
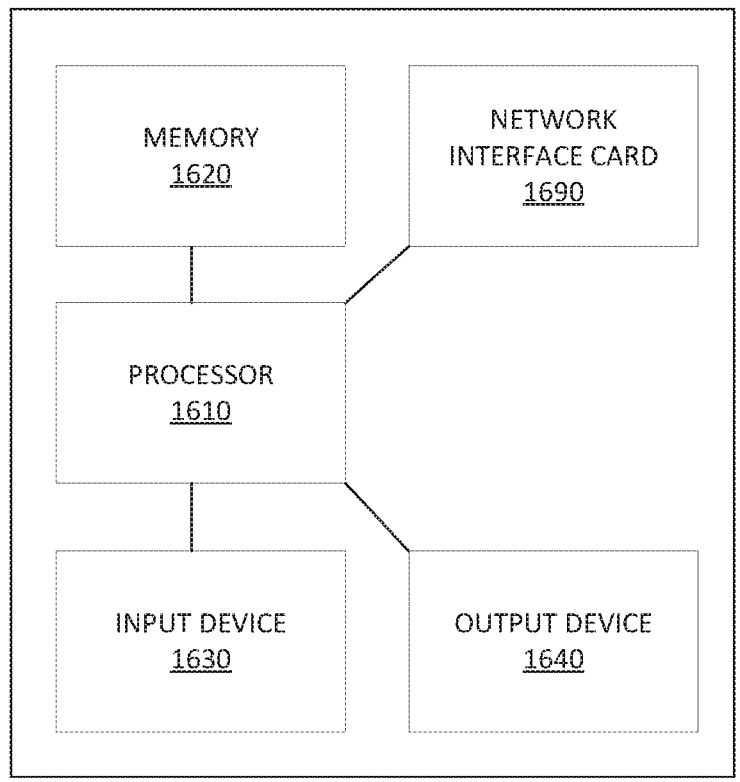
FIG. 16 illustrates a functional block diagram of one example of the computer shown in FIG. 15.

FIG. 16 illustrates a functional block diagram of one example of a computer of FIG. 23. The computer 1502a includes a processor 1610 in data communication with a memory 1620, an input device 1630, and an output device 1640. In some embodiments, the processor is further in data communication with an optional network interface card 1690. Although described separately, it is to be appreciated that functional blocks described with respect to the computer 1502a need not be separate structural elements. For example, the processor 1610 and memory 1620 may be embodied in a single chip.

The processor 1610 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 1610 can be coupled, via one or more buses, to read information from or write information to memory 1620. The processor may additionally, or in the alternative, contain memory, such as processor registers. The memory 1620 can include processor cache, including a multi-level hierarchical cache in which different levels have different capacities and access speeds. The memory 1620 can also include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 1610 also may be coupled to an input device 1630 and an output device 1640 for, respectively, receiving input from and providing output to a user of the computer 1502a. Suitable input devices include, but are not limited to, a keyboard, buttons, keys, switches, a pointing device, a mouse, a joystick, a remote control, an infrared detector, a bar code reader, a scanner, a video camera (possibly coupled with video processing software to, e.g., detect hand gestures or facial gestures), a motion detector, or a microphone (possibly coupled to audio processing software to, e.g., detect voice commands). Suitable output devices include, but are not limited to, visual output devices, including displays and printers, audio output devices, including speakers, headphones, earphones, and alarms, additive manufacturing devices, and haptic output devices.

The processor 1610 further may be coupled to a network interface card 1690. The network interface card 1690 prepares data generated by the processor 1610 for transmission via a network according to one or more data transmission protocols. The network interface card 1690 also decodes data received via a network according to one or more data transmission protocols. The network interface card 1690 can include a transmitter, receiver, or both. In other embodiments, the transmitter and receiver can be two separate components. The network interface card 1690, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein.

Figure 17:
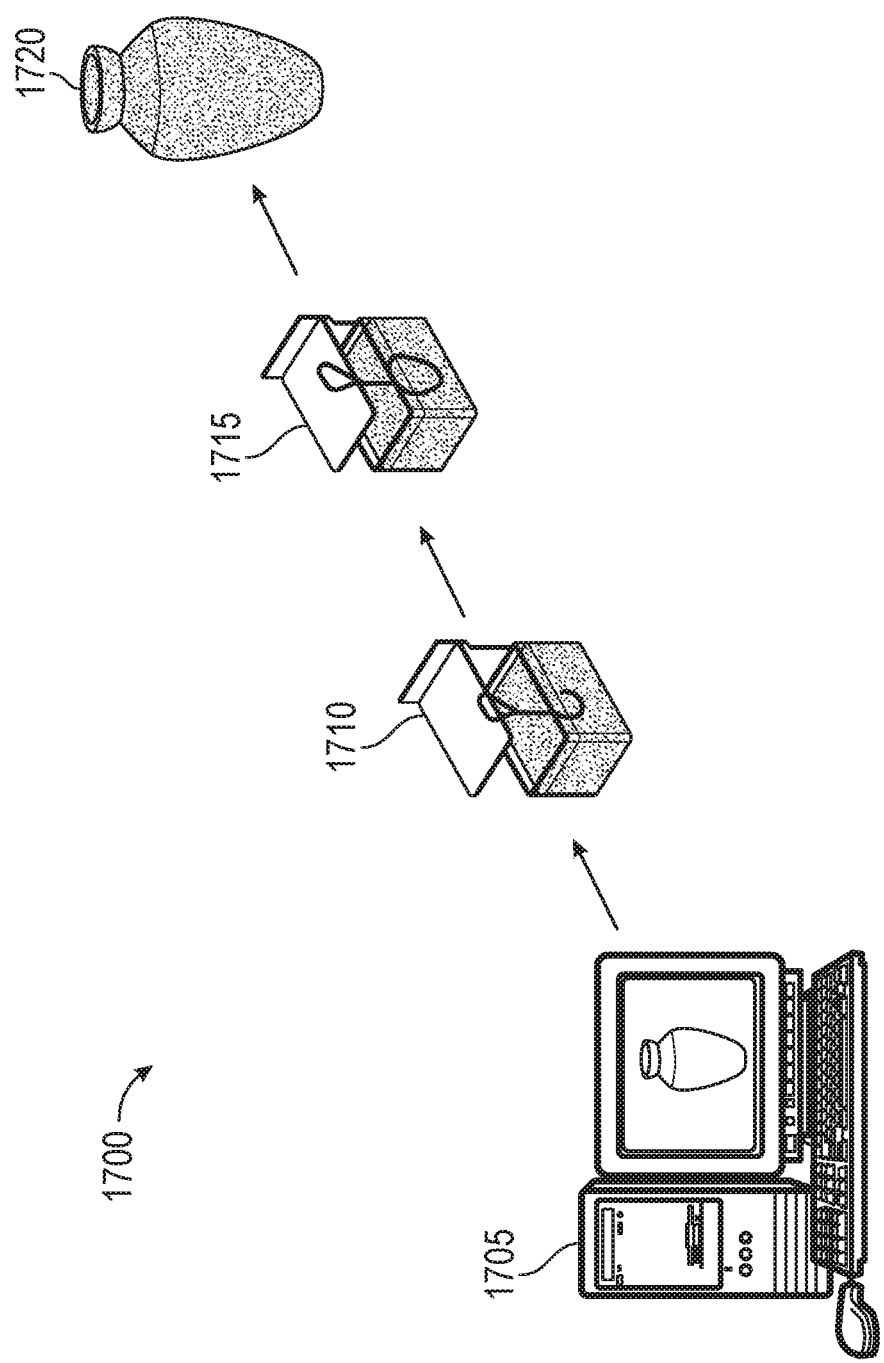
FIG. 17 shows a high-level process for manufacturing a 3D object using an additive manufacturing system.

FIG. 17 illustrates a process 1700 for manufacturing a 3-D object or device. As shown, at a step 1705, a digital representation of the object is designed using a computer, such as the computer 1502a. For example, 2-D or 3-D data may be input to the computer 1502a for aiding in designing the digital representation of the 3-D object. Continuing at a step 1710, information is sent from the computer 1502a to an additive manufacturing device, such as additive manufacturing device 1508a, and the device 1508a commences the manufacturing process in accordance with the received information. At a step 1715, the additive manufacturing device 1508*a* continues manufacturing the 3-D object using suitable materials, such as a liquid resin. At a step 1720, the object is finally built. The object may be any of the objects described herein, such as with respect to FIGS. 1-14.

These suitable materials may include, but are not limited to a photopolymer resin, polyurethane, methyl methacrylate-acrylonitrile-butadiene-styrene copolymer, resorbable materials such as polymer-ceramic composites, metals, metal alloys, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC ISO, PC, ULTEM 9085, PPSF and PPSU materials from Stratasys; Accura Plastic, DuraForm, CastForm, Laserform and VisiJet line of materials from 3D-Systems; the PA line of materials, PrimeCast and PrimePart materials and Alumide and CarbonMide from EOS GmbH, Aluminum, CobaltChrome and Stainless Steel materials, MarangingSteel, Nickel Alloy, Titanium, and Titanium alloys. The VisiJet line of materials from 3-Systems may include Visijet Flex, Visijet Tough, Visijet Clear, Visijet HiTemp, Visijet e-stone, Visijet Black, Visijet Jewel, Visijet FTI, etc. Examples of other materials may include Objet materials, such as Objet Fullcure, Objet Veroclear, Objet Digital Materials, Objet Duruswhite, Objet Tangoblack, Objet Tangoplus, Objet Tangoblackplus, etc. Another example of materials may include materials from the Renshape 5000 and 7800 series. Further, at a step 2520, the 3-D object is generated.

Various embodiments disclosed herein provide for the use of computer software being executed on a computing device. A skilled artisan will readily appreciate that these embodiments may be implemented using numerous different types of computing devices, including both general-purpose and/or special-purpose computing system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

Various embodiments disclosed herein may be implemented using a computer or computer control system. A skilled artisan will readily appreciate that these embodiments may be implemented using numerous different types of computing devices, including both general-purpose and special-purpose computing-system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or nontransitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A fixation device for insertion into bone, the fixation device comprising:
    a body comprising threads along an inner surface of the body;
    one or more blades movably coupled to the body via one or more first hinges;
    a coupling member coupled to the one or more blades via one or more second hinges; and a threaded cap translationally coupled to the coupling member, the threaded cap comprising complementary threads to the threads of the body, wherein:
- the one or more blades are configured to move between at least a first position and a second position;
- in the first position, the one or more blades are retracted into the body;
- in the second position, the one or more blades are deployed out of the body for insertion into the bone,
- the coupling member is configured to move translationally based on a translational force applied by the threaded cap, and
- the threaded cap is configured to move translationally based on a rotational force applied to the threaded cap.

2. The fixation device of claim 1, wherein at least one of the one or more blades comprises a substantially planar puncturing element.

3. The fixation device of claim 2, wherein the at least one of the one or more blades has a triangular shape.

4. The fixation device of claim 1, wherein at least one of the one or more blades comprises a 3D puncturing element.

5. The fixation device of claim 4, wherein the at least one of the one or more blades has a pyramid shape.

6. The fixation device of claim 1, wherein at least one of the one or more blades has a surface area that extends in more than one direction along more than one line path or curve.

7. The fixation device of claim 1, wherein the one or more blades are configured to move between the at least the first position and the second position based on the translational movement of the coupling member.

8. The fixation device of claim 1, wherein the one or more blades are coupled to the coupling member via a connecting member.

9. The fixation device of claim 1, wherein the coupling member is not rotationally coupled to the threaded cap.

10. The fixation device of claim 1, wherein the body comprises a porous structure.

11. The fixation device of claim 1, wherein the fixation device comprises a lag screw of a dynamic hip screw system.

12. The fixation device of claim 1, wherein the one or more blades being movably coupled to the body comprises the one or more blades being coupled by an elastically deforming member.

13. The fixation device of claim 1, wherein the body comprises one or more openings, and wherein the one or more blades are configured to move through the one or more openings.

14. The fixation device of claim 1, wherein the body comprises additional threads along an outer surface of the body.

* * * * *